(12) United States Patent
Heidecke et al.

(10) Patent No.: US 10,203,343 B2
(45) Date of Patent: Feb. 12, 2019

(54) DIAGNOSIS OF CANCER BY DETECTING AUTO-ANTIBODIES AGAINST EPIDERMAL GROWTH FACTOR (EGF)

(71) Applicant: CELLTREND GMBH, Luckenwalde (DE)

(72) Inventors: Harald Heidecke, Berlin (DE); Kai Schulze-Forster, Berlin (DE)

(73) Assignee: CELLTREND GMBH, Luckenwalde (DE)

( * ) Notice: Subject to any disclaimer, the term of this patent is extended or adjusted under 35 U.S.C. 154(b) by 0 days.

(21) Appl. No.: 15/116,476

(22) PCT Filed: Feb. 3, 2015

(86) PCT No.: PCT/EP2015/052182
§ 371 (c)(1),
(2) Date: Aug. 3, 2016

(87) PCT Pub. No.: WO2015/117952
PCT Pub. Date: Aug. 13, 2015

(65) Prior Publication Data
US 2017/0010287 A1   Jan. 12, 2017

(30) Foreign Application Priority Data
Feb. 4, 2014 (EP) .................................. 14153822

(51) Int. Cl.
| G01N 33/74 | (2006.01) |
| G01N 33/564 | (2006.01) |
| G01N 33/574 | (2006.01) |

(52) U.S. Cl.
CPC .......... *G01N 33/74* (2013.01); *G01N 33/564* (2013.01); *G01N 33/57449* (2013.01); *G01N 2333/485* (2013.01); *G01N 2800/52* (2013.01)

(58) Field of Classification Search
None
See application file for complete search history.

(56) References Cited

U.S. PATENT DOCUMENTS

2003/0104014 A1   6/2003   Casimiro et al.

FOREIGN PATENT DOCUMENTS

| WO | 2005016126 A2 | 2/2005 |
| WO | 2005043165 A2 | 5/2005 |

OTHER PUBLICATIONS

Gonzalez, et al., "Epidermal growth factor-based cancer vaccine for non-small-cell lung cancer therapy", 2003 European Society for Medical Oncology, Annals of Oncology 14 :461-466, 2003 DOI: 10.1093/annone/mdg 102.
Nolen, et al. "Aberrant turmor-associated antigen autoantibody profiles in healthy controls detected by multiplex bead-based immunoassay", 2009 Elsevier B.V. Journal of Immunological Methods 344 (2009) pp. 116-120.
Gonzalez, et al., "Induction of Immune Recognition of Self Epidermal Growth Factor (EGF): Effect on EGF-Biodistribution and Tumor Growth", Vaccine Research, vol. 5, No. 4, 1996, Mary Ann Liebert, Inc; pp. 233-244.
Rodriguez, et al., "Therapeutic vaccination with an EGF-based vaccine in lung cancer: a step in the transition to a chronic disease", 2011 Expert Reviews Ltd., Expert Rev. Respir. Med 5(3), 337-342 (2011).
EP 15702481.1 Communication pursuant to Article 94(3) EPC dated Aug. 8, 2017; pp. 6.
Baron A., et al., "Serum EGF and soluble ErbB1 levels as tumor biomarkers in women with stage III or IV epithelial ovarian cancer", Proceedings of the American Association for Cancer Research Annual Meeting; vol. 40; Mar. 1999 (Mar. 1999); p. 43; XP818541.

*Primary Examiner* — Marianne P Allen
(74) *Attorney, Agent, or Firm* — Morris, Manning & Martin, LLP; Daniel E. Sineway, Esq.; R. Lee Strasburger, Jr., Esq.

(57) ABSTRACT

The present invention relates to a method for diagnosis of a cancer, comprising the steps of (i) determining the level of antibodies against epidermal growth factor (EGF) in a sample from a subject to be diagnosed, (ii) comparing the determined level in the sample to a control level derived from subjects without cancer; wherein a decreased level in the sample from the subject to be diagnosed as compared to the control level is indicative for cancer in the subject. Furthermore, the invention relates to method of predicting response and outcome of a treatment of a cancer with an epidermal growth factor receptor inhibitor.

9 Claims, 12 Drawing Sheets
Specification includes a Sequence Listing.

A

B

A

B

C

SEQUENCE LISTING

```
<160> NUMBER OF SEQ ID NOS: 2

<210> SEQ ID NO 1
<211> LENGTH: 1166
<212> TYPE: PRT
<213> ORGANISM: Homo sapiens
<220> FEATURE:
<223> OTHER INFORMATION: Amino acid sequence of the human EGF

<400> SEQUENCE: 1

Met Leu Leu Thr Leu Ile Ile Leu Leu Pro Val Val Ser Lys Phe Ser
1               5                   10                  15

Phe Val Ser Leu Ser Ala Pro Gln His Trp Ser Cys Pro Glu Gly Thr
            20                  25                  30

Leu Ala Gly Asn Gly Asn Ser Thr Cys Val Gly Pro Ala Pro Phe Leu
        35                  40                  45

Ile Phe Ser His Gly Asn Ser Ile Phe Arg Ile Asp Thr Glu Gly Thr
    50                  55                  60

Asn Tyr Glu Gln Leu Val Val Asp Ala Gly Val Ser Val Ile Met Asp
65                  70                  75                  80

Phe His Tyr Asn Glu Lys Arg Ile Tyr Trp Val Asp Leu Glu Arg Gln
                85                  90                  95

Leu Leu Gln Arg Val Phe Leu Asn Gly Ser Arg Gln Glu Arg Val Cys
            100                 105                 110

Asn Ile Glu Lys Asn Val Ser Gly Met Ala Ile Asn Trp Ile Asn Glu
        115                 120                 125
```

```
Glu Val Ile Trp Ser Asn Gln Gln Glu Gly Ile Ile Thr Val Thr Asp
    130                 135                 140

Met Lys Gly Asn Asn Ser His Ile Leu Leu Ser Ala Leu Lys Tyr Pro
145                 150                 155                 160

Ala Asn Val Ala Val Asp Pro Val Glu Arg Phe Ile Phe Trp Ser Ser
                165                 170                 175

Glu Val Ala Gly Ser Leu Tyr Arg Ala Asp Leu Asp Gly Val Gly Val
            180                 185                 190

Lys Ala Leu Leu Glu Thr Ser Glu Lys Ile Thr Ala Val Ser Leu Asp
        195                 200                 205

Val Leu Asp Lys Arg Leu Phe Trp Ile Gln Tyr Asn Arg Glu Gly Ser
210                 215                 220

Asn Ser Leu Ile Cys Ser Cys Asp Tyr Asp Gly Gly Ser Val His Ile
225                 230                 235                 240

Ser Lys His Pro Thr Gln His Asn Leu Phe Ala Met Ser Leu Phe Gly
                245                 250                 255

Asp Arg Ile Phe Tyr Ser Thr Trp Lys Met Lys Thr Ile Trp Ile Ala
            260                 265                 270

Asn Lys His Thr Gly Lys Asp Met Val Arg Ile Asn Leu His Ser Ser
        275                 280                 285

Phe Val Pro Leu Gly Glu Leu Lys Val Val His Pro Leu Ala Gln Pro
290                 295                 300

Lys Ala Glu Asp Asp Thr Trp Glu Pro Glu Gln Lys Leu Cys Lys Leu
305                 310                 315                 320

Arg Lys Gly Asn Cys Ser Ser Thr Val Cys Gly Gln Asp Leu Gln Ser
                325                 330                 335

His Leu Cys Met Cys Ala Glu Gly Tyr Ala Leu Ser Arg Asp Arg Lys
            340                 345                 350

Tyr Cys Glu Asp Val Asn Glu Cys Ala Phe Trp Asn His Gly Cys Thr
        355                 360                 365

Leu Gly Cys Lys Asn Thr Pro Gly Ser Tyr Tyr Cys Thr Cys Pro Val
370                 375                 380

Gly Phe Val Leu Leu Pro Asp Gly Lys Arg Cys His Gln Leu Val Ser
385                 390                 395                 400

Cys Pro Arg Asn Val Ser Glu Cys Ser His Asp Cys Val Leu Thr Ser
                405                 410                 415

Glu Gly Pro Leu Cys Phe Cys Pro Glu Gly Ser Val Leu Glu Arg Asp
            420                 425                 430

Gly Lys Thr Cys Ser Gly Cys Ser Ser Pro Asp Asn Gly Gly Cys Ser
        435                 440                 445

Gln Leu Cys Val Pro Leu Ser Pro Val Ser Trp Glu Cys Asp Cys Phe
450                 455                 460

Pro Gly Tyr Asp Leu Gln Leu Asp Glu Lys Ser Cys Ala Ala Ser Gly
465                 470                 475                 480

Pro Gln Pro Phe Leu Leu Phe Ala Asn Ser Gln Asp Ile Arg His Met
                485                 490                 495

His Phe Asp Gly Thr Asp Tyr Gly Thr Leu Leu Ser Gln Gln Met Gly
            500                 505                 510

Met Val Tyr Ala Leu Asp His Asp Pro Val Glu Asn Lys Ile Tyr Phe
        515                 520                 525

Ala His Thr Ala Leu Lys Trp Ile Glu Arg Ala Asn Met Asp Gly Ser
530                 535                 540
```

```
Gln Arg Glu Arg Leu Ile Glu Glu Gly Val Asp Val Pro Glu Gly Leu
545                 550                 555                 560

Ala Val Asp Trp Ile Gly Arg Arg Phe Tyr Trp Thr Asp Arg Gly Lys
                565                 570                 575

Ser Leu Ile Gly Arg Ser Asp Leu Asn Gly Lys Arg Ser Lys Ile Ile
            580                 585                 590

Thr Lys Glu Asn Ile Ser Gln Pro Arg Gly Ile Ala Val His Pro Met
        595                 600                 605

Ala Lys Arg Leu Phe Trp Thr Asp Thr Gly Ile Asn Pro Arg Ile Glu
    610                 615                 620

Ser Ser Ser Leu Gln Gly Leu Gly Arg Leu Val Ile Ala Ser Ser Asp
625                 630                 635                 640

Leu Ile Trp Pro Ser Gly Ile Thr Ile Asp Phe Leu Thr Asp Lys Leu
                645                 650                 655

Tyr Trp Cys Asp Ala Lys Gln Ser Val Ile Glu Met Ala Asn Leu Asp
            660                 665                 670

Gly Ser Lys Arg Arg Leu Thr Gln Asn Asp Val Gly His Pro Phe
        675                 680                 685

Ala Val Ala Val Phe Glu Asp Tyr Val Trp Phe Ser Asp Trp Ala Met
    690                 695                 700

Pro Ser Val Met Arg Val Asn Lys Arg Thr Gly Lys Asp Arg Val Arg
705                 710                 715                 720

Leu Gln Gly Ser Met Leu Lys Pro Ser Ser Leu Val Val Val His Pro
                725                 730                 735

Leu Ala Lys Pro Gly Ala Asp Pro Cys Leu Tyr Gln Asn Gly Gly Cys
            740                 745                 750

Glu His Ile Cys Lys Lys Arg Leu Gly Thr Ala Trp Cys Ser Cys Arg
        755                 760                 765

Glu Gly Phe Met Lys Ala Ser Asp Gly Lys Thr Cys Leu Ala Leu Asp
    770                 775                 780

Gly His Gln Leu Leu Ala Gly Gly Glu Val Asp Leu Lys Asn Gln Val
785                 790                 795                 800

Thr Pro Leu Asp Ile Leu Ser Lys Thr Arg Val Ser Glu Asp Asn Ile
                805                 810                 815

Thr Glu Ser Gln His Met Leu Val Ala Glu Ile Met Val Ser Asp Gln
            820                 825                 830

Asp Asp Cys Ala Pro Val Gly Cys Ser Met Tyr Ala Arg Cys Ile Ser
        835                 840                 845

Glu Gly Glu Asp Ala Thr Cys Gln Cys Leu Lys Gly Phe Ala Gly Asp
    850                 855                 860

Gly Lys Leu Cys Ser Asp Ile Asp Glu Cys Glu Met Gly Val Pro Val
865                 870                 875                 880

Cys Pro Pro Ala Ser Ser Lys Cys Ile Asn Thr Glu Gly Gly Tyr Val
                885                 890                 895

Cys Arg Cys Ser Glu Gly Tyr Gln Gly Asp Gly Ile His Cys Leu Asp
            900                 905                 910

Ser Thr Pro Pro Pro His Leu Arg Glu Asp Asp His His Tyr Ser Val
        915                 920                 925

Arg Asn Ser Asp Ser Glu Cys Pro Leu Ser His Asp Gly Tyr Cys Leu
    930                 935                 940

His Asp Gly Val Cys Met Tyr Ile Glu Ala Leu Asp Lys Tyr Ala Cys
945                 950                 955                 960

Asn Cys Val Val Gly Tyr Ile Gly Glu Arg Cys Gln Tyr Arg Asp Leu
```

-continued

```
                    965                 970                 975
Lys Trp Trp Glu Leu Arg His Ala Gly His Gly Gln Gln Gln Lys Val
            980                 985                 990

Ile Val Val Ala Val Cys Val Val Leu Val Met Leu Leu Leu Leu Leu
            995                1000                1005

Ser Leu Trp Gly Ala His Tyr Tyr Arg Thr Gln Lys Leu Leu Ser Lys
           1010                1015                1020

Asn Pro Lys Asn Pro Tyr Glu Glu Ser Ser Arg Asp Val Arg Ser Arg
1025                1030                1035                1040

Arg Pro Ala Asp Thr Glu Asp Gly Met Ser Ser Cys Pro Gln Pro Trp
           1045                1050                1055

Phe Val Val Ile Lys Glu His Gln Asp Leu Lys Asn Gly Gly Gln Pro
           1060                1065                1070

Val Ala Gly Glu Asp Gly Gln Ala Ala Asp Gly Ser Met Gln Pro Thr
           1075                1080                1085

Ser Trp Arg Gln Glu Pro Gln Leu Cys Gly Met Gly Thr Glu Gln Gly
           1090                1095                1100

Cys Trp Ile Pro Val Ser Ser Asp Lys Gly Ser Cys Pro Gln Val Met
1105                1110                1115                1120

Glu Arg Ser Phe His Met Pro Ser Tyr Gly Thr Gln Thr Leu Glu Gly
                   1125                1130                1135

Gly Val Glu Lys Pro His Ser Leu Leu Ser Ala Asn Pro Leu Trp Gln
           1140                1145                1150

Gln Arg Ala Leu Asp Pro Pro His Gln Met Glu Leu Thr Gln
           1155                1160                1165

<210> SEQ ID NO 2
<211> LENGTH: 53
<212> TYPE: PRT
<213> ORGANISM: Homo sapiens
<220> FEATURE:
<223> OTHER INFORMATION: Amino acid sequence of the human mature EGF
      peptide [amino acids 930 to 982 of SEQ ID NO:1]

<400> SEQUENCE: 2

Asn Ser Asp Ser Glu Cys Pro Leu Ser His Asp Gly Tyr Cys Leu His
1               5                  10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Trp Trp Glu Leu Arg
    50
```

DIAGNOSIS OF CANCER BY DETECTING AUTO-ANTIBODIES AGAINST EPIDERMAL GROWTH FACTOR (EGF)

CROSS-REFERENCE TO RELATED APPLICATIONS

This application is a national stage application under 35 U.S.C. § 371, and claims priority to and the benefit of the filing date of International Application Number PCT/EP2015/052182, filed Feb. 3, 2015, which is herein incorporated in its entirety.

REFERENCE TO A SEQUENCE LISTING SUBMITTED AS A TEXT FILE VIA EFS-WEB

The Sequence Listing submitted Aug. 3, 2016 as a text file named "31904_111943$_{13}$ 2U1$_{13}$ SeqListing.txt", created on Aug. 3, 2016, and having size of 12,288bytes is hereby incorporated by reference pursuant to 37 C.F.R. § 1.52(e)(5).

FIELD OF THE INVENTION

The present invention is in the field of diagnostics, prognosis and therapeutics for cancer, more in particular in the field of diagnosis and therapy of epithelial cancer, more particular in the field of diagnosis, prognosis and therapy of ovarian cancer.

BACKGROUND OF THE INVENTION

According to the American Cancer Society ovarian cancer is expected to account for over 22,000 new cancer diagnoses and more than 14,000 deaths in 2013 in the US alone. Of the gynaecologic malignancies, ovarian cancer has the highest mortality rate. In early stages of the disease, ovarian cancer is nearly asymptomatic. Hence, a large portion of the patients present with clinically advanced stages of ovarian cancer. However, the 5-year survival rate for patients diagnosed with early-stage disease is often >90%, but it is <20% for advanced-stage disease, underscoring the importance of early detection.

Current diagnosis of ovarian cancer relies on pelvic exam, transvaginal ultrasonography, (TVS), abdominal ultrasonography, and exploratory or diagnostic laparoscopy. The most commonly used biomarker for clinical screening and prognosis in patients with ovarian cancer is ovarian cancer antigen 125 (CA125) (Coticchia et al. (2008), J. Natl. Compr. Canc. Netw. 6(8):795-802). Serum CA125 levels are elevated in ≈80% of patients with advanced-stage epithelial ovarian cancer but are increased in only 50-60% of patients with early-stage disease. Serum CA125 levels may be falsely elevated in women with any i.p. pathology resulting in irritation of the serosa of the peritoneum or pericardium, uterine fibroids, renal disorders, and normal menses. Moreover, serum CA125 levels do not predict the outcome of cytoreductive surgery in patients with advanced epithelial ovarian cancer. Further biomarkers include, for example, Human Epidymis Protein 4 (HE4) and Mesothelin (Sarojini et al. (2012), Journal of Oncology 102, Article ID 709049). Severeness of ovarian cancer is categorized by the grade and stage of tumorization. This nowadays can only be performed by evaluation of the tumors under or after surgical treatment or by combining marker evaluation and (histological) evaluation of tissue. Staging is very important because ovarian cancers have different prognosis at different stages and may be treated differently. The accuracy of the staging may determine whether or not a patient will be cured. If the cancer isn't accurately staged, then cancer that has spread outside the ovary might be missed and not treated. Once a stage has been given it does not change, even when the cancer comes back or spreads to new locations in the body.

Ovarian cancer staging is by FIGO staging system uses information obtained after surgery, which can include a total abdominal hysterectomy, removal of (usually) both ovaries and fallopian tubes, (usually) the omentum, and pelvic (peritoneal) washings for cytopathology. The AJCC stage is the same as the FIGO stage. The AJCC staging system describes the extent of the primary tumor (T), the absence or presence of metastasis to nearby lymph Nodes (N), and the absence or presence of distant Metastasis (M).

Stage I Limited to One or Both Ovaries
  IA involves one ovary; capsule intact; no tumor on ovarian surface; no malignant cells in ascites or peritoneal washings
  IB involves both ovaries; capsule intact; no tumor on ovarian surface; negative washings
  IC tumor limited to ovaries with any of the following: capsule ruptured, tumor on ovarian surface, positive washings
Stage II Pelvic Extension or Implants
  IIA extension or implants onto uterus or fallopian tube; negative washings
  IIB extension or implants onto other pelvic structures; negative washings
  IIC pelvic extension or implants with positive peritoneal washings
Stage III Peritoneal Implants Outside of the Pelvis; or Limited to the Pelvis with Extension to the Small Bowel or Omentum
  IIIA microscopic peritoneal metastases beyond pelvis
  IIIB macroscopic peritoneal metastases beyond pelvis less than 2 cm in size
  IIIC peritoneal metastases beyond pelvis >2 cm or lymph node metastases
Stage IV Distant Metastases to the Liver or Outside the Peritoneal Cavity Para-aortic lymph node metastases are considered regional lymph nodes (Stage IIIC). As there is only one para-aortic lymph node intervening before the thoracic duct on the right side of the body, the ovarian cancer can rapidly spread to distant sites such as the lung.

The AJCC/TNM staging system includes three categories for ovarian cancer, T, N and M. The T category contains three other subcategories, T1, T2 and T3, each of them being classified according to the place where the tumor has developed (in one or both ovaries, inside or outside the ovary). The T1 category of ovarian cancer describes ovarian tumors that are confined to the ovaries, and which may affect one or both of them. The sub-subcategory T1a is used to stage cancer that is found in only one ovary, which has left the capsule intact and which cannot be found in the fluid taken from the pelvis. Cancer that has not affected the capsule, is confined to the inside of the ovaries and cannot be found in the fluid taken from the pelvis but has affected both ovaries is staged as T1b. T1c category describes a type of tumor that can affect one or both ovaries, and which has grown through the capsule of an ovary or it is present in the fluid taken from the pelvis. T2 is a more advanced stage of cancer. In this case, the tumor has grown in one or both ovaries and is spread to the uterus, fallopian tubes or other pelvic tissues. Stage T2a is used to describe a cancerous tumor that has spread to the uterus or the fallopian tubes (or both) but which is not present in the fluid taken from the pelvis. Stages T2b and T2c indicate cancer that metastasized to other pelvic tissues than the uterus and fallopian tubes and which cannot be seen in the fluid taken from the pelvis, respectively tumors that spread to any of the pelvic tissues (including uterus and fallopian tubes) but which can also be found in the fluid taken from the pelvis. T3 is the stage used to describe cancer that has spread to the peritoneum. This stage provides information on the size of the metastatic tumors (tumors that are located in other areas of the body, but are caused by ovarian cancer). These tumors can be very small, visible only under the microscope (T3a), visible but not larger than 2 centimeters (T3b) and bigger than 2 centimeters (T3c). This staging system also uses N categories to describe cancers that have or not spread to nearby lymph nodes. There are only two N categories, N0 which indicates that the cancerous tumors have not affected the lymph nodes, and N1 which indicates the involvement of lymph nodes close to the tumor. The M categories in the AJCC/TNM staging system provide information on whether the ovarian cancer has metastasized to distant organs such as liver or lungs. M0 indicates that the cancer did not spread to distant organs and M1 category is used for cancer that has spread to other organs of the body.

The AJCC/TNM staging system also contains a Tx and a Nx sub-category which indicates that the extent of the tumor cannot be described because of insufficient data, respectively the involvement of the lymph nodes cannot be described because of the same reason. The ovarian cancer stages are made up by combining the TNM categories in the following manner:

Stage I: T1+N0+M0; IA: T1a+N0+M0; IB: T1b+N0+M0; IC: T1c+N0+M0;

Stage II: T2+N0+M0; IIa: T2a+N0+M0; IIB: T2b+N0+M0; IIC: T2c+N0+M0;

Stage III: T3+N0+M0; IIIA: T3a+N0+M0; IIIB: T3b+N0+M0; IIIC: T3c+N0+M0 or Any T+N1+M0;

Stage IV: Any T+Any N+M1

In addition to being staged, like all cancers ovarian cancer is also graded. The histologic grade of a tumor measures how abnormal or malignant its cells look under the microscope. There are four grades indicating the likelihood of the cancer to spread and the higher the grade, the more likely for this to occur. Grade 0 is used to describe non-invasive tumors. Grade 0 cancers are also referred to as borderline tumors. Grade 1 tumors have cells that are well differentiated (look very similar to the normal tissue) and are the ones with the best prognosis. Grade 2 tumors are also called moderately well differentiated and they are made up by cells that resemble the normal tissue. Grade 3 tumors have the worst prognosis and their cells are abnormal, referred to as poorly differentiated.

However, there is a need for improved tools for the early detection; staging, grading and prognosis of ovarian cancer.

SUMMARY OF THE INVENTION

Subject of the invention is a method for diagnosis of a cancer, comprising the steps of
(i) determining the level of antibodies against epidermal growth factor (EGF) in a sample from a subject to be diagnosed,
(ii) comparing the determined level in the sample to a control level of antibodies against EGF (EGF antibody control level) derived from subjects without cancer;
wherein a decreased level in the sample from the subject to be diagnosed as compared to the control level is indicative for cancer in the subject.

The invention further pertains to a method for diagnosis of a cancer, wherein the level of antibodies against epidermal growth factor (EGF) is determined in a sample from a subject to be diagnosed and wherein a level of anti-EGF antibodies below 60 units/ml is indicative for cancer, preferably below 55 units/ml, more preferably below 50 units/ml, even more preferred below 47 units/ml, further preferred levels indicative for cancer are below 45 units/ml.

The present invention is further directed to an immunoassay method for detecting an anti-EGF antibody in a sample from a subject, comprising the steps of
(a) contacting the sample suspected of comprising an anti-EGF antibody with epidermal growth factor (EGF) or an antigenic peptide fragment thereof under conditions allowing for the formation of a complex between the anti-EGF antibody with EGF or the peptide fragment thereof,
(b) detecting the complex.

In the context of the present invention EGF or an antigenic peptide fragment thereof can thus be used for the diagnosis of cancer.

The present invention further relates to research and/or diagnostic kit for the diagnosis of cancer or for the prediction of response or non-response in a patient, wherein the kit comprises epidermal growth factor (EGF) or an antigenic (immunogenic) peptide fragment thereof.

The inventors also found that the level of antibodies against epidermal growth factor (EGF) correlates with the risk of relapse or mortality in subjects treated with a monoclonal antibody directed against EGFR. Decreased levels of anti-EGF antibodies in samples correlated with a higher risk of relapse and/or mortality in patients treated with said monoclonal antibody. Hence, levels of anti-EGF antibodies in samples of patients to be treated with inhibitor of EGFR activity are an indicator for response or non-response of a patient, i.e. whether improvement of the disease is achieved in a patient (responder) or not (non-responder). If a patient responds to a treatment the disease is ameliorated. It might be the case that a patient responds to a treatment at first but suffers from relapse of the disease at a later stage. Also this is a form of non-response. However, it is difficult to predict whether a patient will respond or not to a treatment as it may be determined only at later stages with the known methods, e.g. when relapse, progression or death occurs. This problem is solved by the present invention as it provides a predictive method to predict whether a subject will respond or not to a certain treatment, e.g. a treatment with an inhibitor of EGFR activity.

Therefore, the invention also relates to a method for determining whether a subject being treated or to be treated for cancer with a drug will respond to said treatment comprising the steps of
(i) determining the level of antibodies against epidermal growth factor (EGF) in a sample from said subject being treated or to be treated with a drug,
(ii) comparing the determined level in the sample to either one or both of a first and second EGF antibody control level, wherein
  a) the first EGF antibody control level is derived from subjects responding to said treatment, and
  b) the second EGF antibody control level is derived from a subject not responding to said treatment,
wherein a decreased level in the sample from the subject being treated or to be treated as compared to the first EGF antibody control level and/or an equal level as compared to the second EGF antibody control level is indicative for a non-response of said subject to said treatment, and wherein an increased level in the sample from the subject being treated or to be treated as compared to the second EGF antibody control level and/or an equal level as compared to the first EGF antibody control level is indicative for a response of said subject to said treatment. In a preferred embodiment of the invention the subject is to be treated, i.e. the method to determine response of a subject is performed before the onset of treatment. In a preferred embodiment the drug is an inhibitor of EGFR activity according to the present invention. Furthermore, ratios may be used in order to determine response or non-response to a treatment with a drug, preferably panitumumab. In such embodiment a level of antibodies against EGF in the sample from the subject to be treated of less than 0.9 fold as compared to the first EGF antibody control level is indicative for a non-response of said subject to said treatment, preferably a level of antibodies against EGF in the sample from the subject to be treated of less than 0.6 fold as compared to the first EGF antibody control level is indicative for a non-response of said subject to said treatment, further preferred a level of antibodies against EGF in the sample from the subject to be treated of less than 0.5 fold as compared to the first anti-EGF control level is indicative for a non-response of said subject to said treatment. Likewise, ratios may be determined for the response. In such embodiment a level of antibodies against EGF in the sample from the subject to be treated of more than 1.5 fold as compared to the second EGF antibody control level is indicative for a response of said subject to said treatment, preferably a level of antibodies against EGF in the sample from the subject to be treated of more than 1.9 fold as compared to the second EGF antibody control level is indicative for a response of said subject to said treatment, further preferred a level of antibodies against EGF in the sample from the subject to be treated of more than 2.0 fold as compared to the second anti-EGF control level is indicative for a response of said subject to said treatment. The treatment and response preferably relate to an inhibitor of EGFR activity as defined herein, preferably panitumumab.

The present invention also relates to a method of treating cancer in a subject, comprising determining the level of antibodies against epidermal growth factor (EGF) in a sample from the subject, wherein when the level of anti-EGF antibodies in a sample from the subject is above 60 units/ml, a drug is administered to the subject, preferably at levels above 65 units/ml, further preferred above 70 units/ml, also preferred at levels above 80 units/ml. However, the threshold may also be determined as outlined above, hence, the method of treating cancer in a subject may also comprise the method for determining whether a subject being treated or to be treated for cancer with a drug, preferably said drug is an inhibitor of EGFR activity, will respond to said treatment, wherein the inhibitor of EGFR activity is administered if the determined levels of EGF antibodies in said subject is indicative for response to the inhibitor of EGFR activity.

As outlined herein, results of non-response of a patient to a treatment may be relapse of cancer, death (mortality) or progression of the cancer. Hence, in a preferred embodiment of the method to determine/predict the response of a subject to a treatment the present invention also relates to a method for the prediction of risk stratification for relapse of cancer and/or mortality in a patient being treated or to be treated with a drug, the method comprising the steps of (i) determining the level of antibodies against epidermal growth factor (EGF) in a sample from said subject being treated or to be treated for cancer with a drug (ii) comparing the determined level in the sample to either one or both of a first and a second EGF antibody control level, a) wherein the first EGF antibody control level is derived from subjects not showing relapse of cancer or mortality after treatment with said drug, and b) wherein the second EGF antibody control level is derived from subjects showing relapse of cancer or mortality after treatment with said drug, wherein a decreased level in the sample from the subject being treated as compared to the first EGF antibody control level and/or an equal level as compared to the second EGF antibody control level is indicative for relapse or progression of cancer or mortality in the subject; and wherein a increased level in the sample from the subject being treated as compared to the second EGF antibody control level and/or an equal level as compared to the first EGF antibody control level is indicative for no relapse, no progression of cancer and no mortality in the subject. Preferably the level in said patient is determined before the onset of treatment. The preferred subject is therefore in this context a subject to be treated with said drug. In a preferred embodiment of the present invention first EGF antibody control level is derived from subjects that did not show relapse or progression of cancer or mortality within 6 months after onset of treatment with said drug and the second EGF antibody control level is derived from subjects that did show relapse or progression of cancer or mortality within 6 months after onset of treatment with said drug.

As will be readily understood by the skilled person, this method may be performed as a method for monitoring treatment efficiency. In this embodiment the levels of anti-EGF antibodies in said subject is determined during treatment, i.e. in a subject being treated with said drug.

DETAILED DESCRIPTION OF THE INVENTION

The present invention is based on the surprising finding of the inventors that in samples of patients with cancer (e.g ovarian cancer) decreased levels of anti-EGF antibodies can be found as compared to subjects without cancer. In other words the inventors have found that patients with cancer have little or no detectable antibodies against epidermal growth factor (EGF) in the blood (e.g. determined in serum) whereas in control groups anti-EGF auto-antibodies can be detected at higher levels.

The present invention is based on the finding of that levels of autoimmune-antibodies in subjects have diagnostic and predictive properties. The antibodies to be detected in connection with the present invention are therefore autoantibody, i.e. those produced by immune system of the subject to be diagnosed or being or to be treated.

The invention relates to a method for the diagnosis of a cancer, comprising the steps of
(i) determining the level of antibodies against EGF in a sample from a subject to be diagnosed,
(ii) comparing the determined level in the sample to a control level derived from subjects without cancer;
wherein a decreased level in the sample from the subject to be diagnosed as compared to the control level is indicative for cancer in the subject. Preferably, the cancer is an EGFR or EGF associated cancer, preferably selected from the group consisting of ovarian cancer, colorectal cancer, colon cancer, lung cancer, ovarian cancer, breast cancer, glioblastoma, kidney (renal) cancer pancreatic cancer, liver cancer, prostate cancer, and gastric cancer, preferably ovarian cancer. It will be understood by those of ordinary skills in the art, that if a preferred cancer is chose to be diagnosed, the control level should be derived from subjects without that specific cancer, i.e. if ovarian cancer is to be diagnosed, the control level shall be derived from subjects without ovarian cancer.

Figure 1:
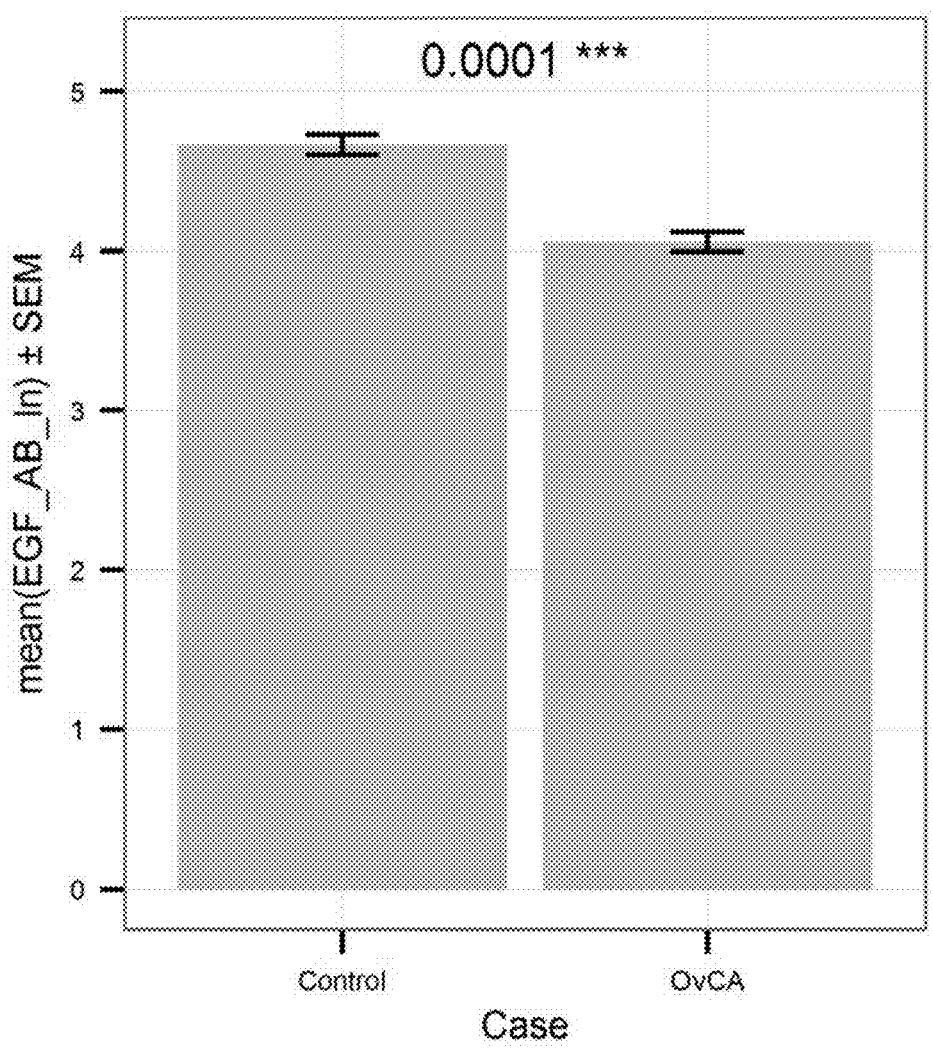
FIG. 1: Comparison of the ln of mean level of anti-EGF antibodies (ln of units/ml) in serum samples of ovarian cancer patients (OvCA; ln of mean=4.058; n=201) to the ln of mean level of anti-EGF antibodies in serum samples of a healthy control group (Control, ln of mean=4.667 units/ml; n=132). The p-value is indicated on top. Bars indicate standard error of mean.

As can be derived from FIG. 1, the ln of the mean level of EGF antibodies in patients suffering from ovarian cancer is 4.058 (=57.86 units/ml) and in healthy subjects 4.667 (=106.38 units/ml). Hence, in one embodiment a level of less than 0.9 fold as compared to the control level from subjects without cancer is indicative for the presence of cancer, preferably a level of less than 0.8 fold, more preferably of less than 0.7 fold, even more preferred of less than 0.6 fold. The cancer is preferably a EGF or EGFR driven cancer as defined herein. Particularly preferred is ovarian cancer. The skilled person will acknowledge that in case a certain cancer is to be diagnosed, the control level is preferably derived from subjects not having this particular cancer.

Auto-antibodies directed against EGF are not known until today. The inventors of the present application for the first time demonstrate the presence of such antibodies as well as the diagnostic and predictive value. It was found that a decrease in the level of antibodies directed against EGF in samples of a subject to be diagnosed as compared samples from subjects with proven absence of cancer is indicative for the presence of cancer as well as for the prediction of response or non-response to a treatment of the cancer with a drug. Hence, "cancer" in connection with the present invention is to be understood as any diseases involving unregulated cell growth. Cancer in this regard is a disease where cells divide and grow uncontrollably resulting in the formation of malignant tumors. However, in a preferred embodiment of the present invention "cancer" refers to an EGF or EGF-receptor (EGFR) associated cancer. EGF and EGFR associated cancers are known by the skilled person. Mutations that lead to EGF overexpression (known as upregulation) or overactivity have been associated with a number of cancers, including lung cancer, anal cancers (Walker F, Abramowitz L, Benabderrahmane D, Duval X, Descatoire V, Hénin D, Lehy T, Aparicio T (November 2009). "Growth factor receptor expression in anal squamous lesions: modifications associated with oncogenic human papillomavirus and human immunodeficiency virus". Hum. Pathol. 40 (11): 1517-27), ovarian cancer and glioblastoma multiforme. Mutations involving EGFR could lead to its constant activation, which could result in uncontrolled cell division—a predisposition for cancer (Lynch T J, Bell D W, Sordella R, Gurubhagavatula S, Okimoto R A, Brannigan B W, Harris P L, Haserlat S M, Supko J G, Haluska F G, Louis D N, Christiani D C, Settleman J, Haber D A (May 2004). "Activating mutations in the epidermal growth factor receptor underlying responsiveness of non-small-cell lung cancer to gefitinib". N. Engl. J. Med. 350 (21): 2129-39). Mutations, amplifications or misregulations of EGFR or family members are implicated in about 30% of all epithelial cancers. Missregulation of EGFR also occurs via missregulation of EGF. Hence, in a preferred embodiment of the present invention the cancer is an epithelial cancer, preferably selected from the group consisting of ovarian cancer, colorectal cancer, colon cancer, lung cancer, ovarian cancer, breast cancer, glioblastoma, kidney (renal) cancer pancreatic cancer, liver cancer, prostate cancer, and gastric cancer, preferably ovarian cancer. In a particularly preferred embodiment the cancer according to the present invention, including all embodiments, is an ovarian cancer.

In the context of the present invention the subject to be diagnosed is a mammal. In a further preferred embodiment the subject is a female mammal, preferably a female human subject suspected of having ovarian cancer or a female mammal, preferably a female human subject to be screened for the presence of ovarian cancer, preferably a female human subject to be treated or being treated for ovarian cancer with a drug.

The invention particularly relates to a method for diagnosis of a cancer, wherein the level of antibodies against EGF is determined in a sample from a subject to be diagnosed and wherein a level of anti-EGF antibodies below 60 units/ml is indicative for ovarian cancer, preferably below 55 units/ml, more preferably below 50 units/ml, even more preferred below 47 units/ml, further preferred levels indicative for ovarian cancer are below 45 units/ml.

In the context of the present invention the terms "EGF" relates to the "epidermal growth factor", while "EGFR" or "EGF receptor" relate to "epidermal growth factor receptor" (also known as"ErbB-1" and "HER1").

Epidermal growth factor (EGF) is a growth factor stimulating cell growth, proliferation, and differentiation by binding to its receptor EGFR. The Human EGF is a 6045 Da protein (Harris R C, Chung E, Coffey R J (March 2003). "EGF receptor ligands". Experimental Cell Research 284 (1): 2-13) with 53 amino acid residues and three intramolecular disulfide bonds (Carpenter G, Cohen S (May 1990). "Epidermal growth factor". The Journal of Biological Chemistry 265 (14): 7709-12). EGF results in cellular proliferation, differentiation, and survival (Herbst R S (2004). "Review of epidermal growth factor receptor biology". International Journal of Radiation Oncology, Biology, Physics 59 (2 Suppl): 21-6). EGF is a low-molecular-weight polypeptide first purified from the mouse submandibular gland, but since then found in many human tissues including submandibular gland, parotid gland. Salivary EGF, which seems also regulated by dietary inorganic iodine, also plays an important physiological role in the maintenance of oroesophageal and gastric tissue integrity. The biological effects of salivary EGF include healing of oral and gastroesophageal ulcers, inhibition of gastric acid secretion, stimulation of DNA synthesis as well as mucosal protection from intraluminal injurious factors such as gastric acid, bile acids, pepsin, and trypsin and to physical, chemical and bacterial agents (Venturi S.; Venturi M. (2009). "Iodine in evolution of salivary glands and in oral health". Nutrition and Health 20 (2): 119-134). Increased activity of the receptor for EGF has been observed in certain types of cancer, often correlated with mutations in the receptor and abnormal function such as constitutive receptor signalling independent of the levels of EGF or of binding of EGF (Lurje G., et al. (2009), "EGFR Signalling and Drug Discovery", Oncology 77: 400-410). Pharmaceutical drugs developed for inhibiting the EGF receptor include Gefitinib and Erlotinib for lung cancer, and Cetuximab for colon cancer. Monoclonal antibodies are potential substances for this purpose.

The epidermal growth factor receptor is a member of the ErbB family of receptors, a subfamily of four closely related receptor tyrosine kinases: EGFR (ErbB-1), HER2/c-neu (ErbB-2), Her 3 (ErbB-3) and Her 4 (ErbB-4). Mutations affecting EGFR expression or activity could result in cancer (Zhang H, Berezov A, Wang Q, Zhang G, Drebin J, Murali R, Greene M I (August 2007). "ErbB receptors: from oncogenes to targeted cancer therapies". J. Clin. Invest. 117 (8): 2051-8).

EGFR (epidermal growth factor receptor) exists on the cell surface and is activated by binding of its specific ligands, including epidermal growth factor and transforming growth factor α (TGFα). ErbB2 has no known direct activating ligand, and may be in an activated state constitutively or become active upon heterodimerization with other family members such as EGFR. Upon activation by its growth factor ligands, EGFR undergoes a transition from an inactive monomeric form to an active homodimer (Yosef Yarden and Joseph Schlessinger (1987). "Epidermal Growth-Factor Induces Rapid, Reversible Aggregation of the Purified Epidermal Growth-Factor Receptor". Biochemistry 26 (5): 1443-1451). In addition to forming homodimers after ligand binding, EGFR may pair with another member of the ErbB receptor family, such as ErbB2/Her2/neu, to create an activated heterodimer. Formation of clusters of activated EGFRs have been reported, although it remains unclear whether this clustering is important for activation itself or if it is a secondary effect occurring after activation by dimerization.

EGFR dimerization stimulates its intrinsic intracellular protein-tyrosine kinase activity and autophosphorylation of tyrosine (Y) residues in the C-terminal domain of EGFR occurs, e.g. Y992, Y1045, Y1068, Y1148 and Y1173 (Downward J, Parker P, Waterfield M D (1984). "Autophosphorylation sites on the epidermal growth factor receptor". Nature 311 (5985): 483-5). Thereby downstream activation and signaling is activated by binding of other proteins to the phosphorylated tyrosines through their phosphotyrosine-binding SH2 domains. These downstream signaling proteins initiate several signal transduction cascades, principally the MAPK, Akt and JNK pathways, leading to DNA synthesis and cell proliferation (Oda K, Matsuoka Y, Funahashi A, Kitano H (2005). "A comprehensive pathway map of epidermal growth factor receptor signaling". Mol. Syst. Biol. 1 (1): 2005.0010). Such proteins modulate phenotypes such as cell migration, adhesion, and proliferation. Activation of the receptor is important for the innate immune response in human skin. The kinase domain of EGFR can also cross-phosphorylate tyrosine residues of other receptors it is aggregated with, and can itself be activated in that manner.

The identification of EGFR as an oncogene has led to the development of anticancer therapeutics directed against EGFR, including gefitinib (Paez J G, Jänne P A, Lee J C, Tracy S, Greulich H, Gabriel S, Herman P, Kaye F J, Lindeman N, Boggon T J, Naoki K, Sasaki H, Fujii Y, Eck M J, Sellers W R, Johnson B E, Meyerson M (June 2004). "EGFR mutations in lung cancer: correlation with clinical response to gefitinib therapy". Science 304 (5676): 1497-500), erlotinib, and cetuximab. Most of the therapeutic approaches target the misregulation of EGFR, i.e. inhibit EGFR activation. Cetuximab and panitumumab are examples of monoclonal antibody inhibitors used for treatment. Other monoclonal antibodies in clinical development are zalutumumab, nimotuzumab, and matuzumab. The monoclonal antibodies block the extracellular ligand binding domain. With the binding site blocked, signal molecules can no longer attach there and activate the tyrosine kinase.

Another method is using small molecules to inhibit the EGFR tyrosine kinase domain at the intracellular part. Without kinase activity, EGFR is unable to activate itself, which is a prerequisite for binding of downstream adaptor proteins. Ostensibly by halting the signaling cascade in cells that rely on this pathway for growth, tumor proliferation and migration is diminished. Gefitinib, erlotinib, and lapatinib (mixed EGFR and ERBB2 inhibitor) are examples of small molecule kinase inhibitors. There are several quantitative methods available that use protein phosphorylation detection to identify EGFR family inhibitors (Olive D M (October 2004). "Quantitative methods for the analysis of protein phosphorylation in drug development". Expert Rev Proteomics 1 (3): 327-41). New drugs such as gefitinib and erlotinib directly target the EGFR. Patients have been divided into EGFR-positive and EGFR-negative, based upon whether a tissue test shows a mutation. EGFR-positive patients have shown a 60% response rate, which exceeds the response rate for conventional chemotherapy. However, clear prediction of the response of a patient to a treatment is still an issue (Jackman D M, Miller V A, Cioffredi L A, Yeap B Y, Janne P A, Riely G J, Ruiz M G, Giaccone G, Sequist L V, Johnson B E (August 2009). "Impact of epidermal growth factor receptor and KRAS mutations on clinical outcomes in previously untreated non-small cell lung cancer patients: results of an online tumor registry of clinical trials". Clin. Cancer Res. 15 (16): 5267-73). Many patients develop resistance increasing the risk for relapse of cancer after treatment. Two primary sources of resistance are the T790M Mutation and MET oncogenes (Jackman et al (2009)). However, as of 2010 there was no consensus of an accepted approach to combat resistance nor FDA approval of a specific combination. Preclinical results have been reported for AP26113 which targets the T790M mutation.

In the context of the immunoassays of the present invention the "EGF" may be present in its natural cellular environment and can be used together with the material associated with EGF in its natural state as well as in isolated form with respect to its primary, secondary and tertiary structures. The EGF is well known to those skilled in the art. The factor is preferably used in isolated form, i.e. essentially free of other proteins, lipids, carbohydrates or other substances naturally associated with the receptor. "Essentially free of" means that the factor is at least 75%, preferably at least 85%, more preferably at least 95% and especially preferably at least 99% free of other proteins, lipids, carbohydrates or other substances naturally associated with the factor.

In connection with the present invention, the naturally occurring factor as well as all modifications, mutants or derivatives of the EGF can be used. Similarly, a EGF produced by means of recombinant techniques, which includes amino acid modifications, such as inversions, deletions, insertions, additions etc. can be used according to the invention provided that this part of the essential function of the EGF is present, namely the capability of binding antibodies. The EGF being used may also comprise exceptional amino acids and/or modifications of such as alkylation, oxidation, thiol-modification, denaturation, oligomerization and the like. The EGF can also be synthesized by chemical means. According to the invention the EGF particularly can be a protein and/or peptide or a fusion protein, which in addition to other proteins, peptides or fragments thereof, includes the EGF as a whole or in part. Using conventional methods, peptides or polypeptides of the EGF which have functionally analogs, analogous properties can be determined by those skilled in the art. For example such polypeptides or peptides have 50-60%, 70% or 80%, preferably 90%, more preferably 95%, and most preferably 98% sequence homology to peptides identified as EGF, and said homology can be determined, e.g. by means of Smith-Waterman homology search algorithm, using the MPFRCH program (Oxford Molecular), for example.

The term "peptide" or "polypeptide" of an EGF used in the present invention, comprises also molecules differing from the original sequence by deletion(s), insertion(s), substitution(s) and/or other modifications well known in the prior art and/or comprising a fragment of the original amino acid molecule, the EGF still exhibiting the properties mentioned above. Such a peptide has preferably at least a length of 100 amino acid residues but may also be shorter, e.g. at least 12, 15, 20 or 25 amino acid residues in length. Also included are allele variants and modifications. Methods of producing the above changes in the amino acid sequence are well known to those skilled in the art and have been described in the standard textbooks of molecular biology, e.g. Sambrook et al., supra. Those skilled in the art will also be able to determine whether an EGF, thus, modified still has the properties mentioned above. The amino acid sequence of EGF is known. Database entries exist in several well known Databases. When refereeing to the amino acid sequence of EGF any amino acid sequence known is meant, particularly those disclosed in common databases, preferably of human origin. The gene which encodes the epidermal growth factor encodes for a larger protein. The encoded protein is synthesized as a large precursor molecule that is proteolytically cleaved to generate the 53-amino acid epidermal growth factor peptide. Dysregulation of this gene has been associated with the growth and progression of certain cancers. Alternate splicing results in multiple transcript variants. The protein encoded by the EGF gene is set out as SEQ ID NO: 1. A preferred sequence of EGF is given as SEQ ID NO:1. The EGF may be glycosylated in vivo. In the present specification all of the above illustrated modifications of the EGF will be referred to as "functionally analogous peptides or proteins" in brief. In a preferred embodiment EGF refers to the mature epithelial growth factor peptide which is cleaved from the propreprotein set out as SEQ ID NO: 1, i.e. amino acids 930 to 982 of SEQ ID NO: 1. The mature EGF peptide is set out as SEQ ID NO: 2 and is a preferred embodiment of EGF according to the present invention.

The antibodies to be detected or determined according to the present invention are directed against EGF. This means that the antibodies specifically bind EGF. Specific binding of an antibody normally occurs via binding of a binding site of the antigen. The antibodies of the present invention are those specifically binding to EGF or immunogenic fragments thereof. This binding may occur via recognition of sequence or structural epitopes. The skilled person is aware of methods of how to determine specific epitopes, e.g. fragments of the antigen EGF-receptor, which are recognized and bound by the antibodies to be determined. Fragments of EGF-receptor binding to the auto antibodies are called immunogenic or antigenic fragments. Methods for determining fragments of an antigen binding the antibody are described in several publications (e.g. Gershoni, J M; Roitburd-Berman, A; Siman-Tov, D D; Tarnovitski Freund, N; Weiss, Y (2007). "Epitope mapping: The first step in developing epitope-based vaccines". BioDrugs 21 (3): 145-56; Westwood, M R; Hay, F C (2001). Epitope Mapping: a practical approach. Oxford, Oxfordshire: Oxford University Press. ISBN 0-19-963652-4; Flanagan et al. (2011), "Mapping Epitopes with H/D-Ex Mass Spec". Genetic Engineering and Biotechnology news; 31(1); Gaseitsiwe, S.; Valentini, D.; Mandavifar, S.; Reilly, M.; Ehrnst, A.; Maeurer, M. (2009) "Peptide Microarray-Based Identification of *Mycobacterium tuberculosis* Epitope Binding to HLA-DRB1*0101, DRB1*1501, and DRB1*0401". Clinical and Vaccine Immunology 17 (1): 168-75; Linnebacher, Michael; Lorenz, Peter; Koy, Cornelia; Jahnke, Annika; Born, Nadine; Steinbeck, Felix; Wollbold, Johannes; Latzkow, Tobias et al. (2012). "Clonality characterization of natural epitope-specific antibodies against the tumor-related antigen topoisomerase IIa by peptide chip and proteome analysis: A pilot study with colorectal carcinoma patient samples" Analytical and Bioanalytical Chemistry 403 (1): 227-38; Cragg, M. S. (2011). "CD20 antibodies: Doing the time warp". Blood 118 (2): 219-20; Banik, Soma S. R.; Doranz, Benjamin J. (2010). "Mapping Complex Antibody Epitopes". Genetic Engineering and Biotechnology News 3 (2): 25-8; and Paes, Cheryl; Ingalls, Jada; Kampani, Karan; Sulli, Chidananda; Kakkar, Esha; Murray, Meredith; Kotelnikov, Valery; Greene, Tiffani A. et al. (2009). "Atomic-Level Mapping of Antibody Epitopes on a GPCR". Journal of the American Chemical Society 131 (20): 6952-4). In context with the present invention EGF antibodies are understood as any immunoglobulin specifically recognizing/binding to EGF, preferably EGF of SEQ ID NO:1 or an immunogenic peptide fragment thereof, preferably the antibodies determined is able to bind to mature EGF of SEQ ID NO:2, preferably it binds to mature EGF of SEQ ID NO:2.

In the context of the present invention the anti-EGF antibody may particularly be selected from the group of IgA-antibody, IgG-antibody and IgM-antibody, preferably an IgG antibody, e.g. IgG1, IgG2, IgG3 and IgG4.

Herein, the sample of the subject to be diagnosed in which the level of anti-EGF antibodies is to be determined is preferably a bodily fluid such as whole blood or lymph or fractions of blood such as serum or plasma. Preferably in the context of the present invention the sample is plasma or serum.

Where appropriate, the sample may need to be homogenized, or extracted with a solvent prior to use in the present invention in order to obtain a liquid sample. A liquid sample hereby may be a solution or suspension. Liquid samples may be subjected to one or more pre-treatments prior to use in the present invention. Such pre-treatments include, but are not limited to dilution, filtration, centrifugation, concentration, sedimentation, precipitation, dialysis. Pre-treatments may also include the addition of chemical or biochemical substances to the solution, such as acids, bases, buffers, salts, solvents, reactive dyes, detergents, emulsifiers, chelators.

The control levels as disclosed herein refer to control levels of EGF antibodies. It will be readily understood by the skilled person that the control levels from subjects having the desired disease or response as defined in the methods and to which the determined levels are compared to, are not necessarily determined in parallel but may be represented by previously determined levels. Nevertheless, control levels may be determined in parallel. The skilled person with the disclosure of the present invention and his knowledge is able to determine such levels, as will be outlined herein below. Hence, the control levels of the present invention may be previously defined thresholds. Preferred thresholds are disclosed herein.

Figure 6:
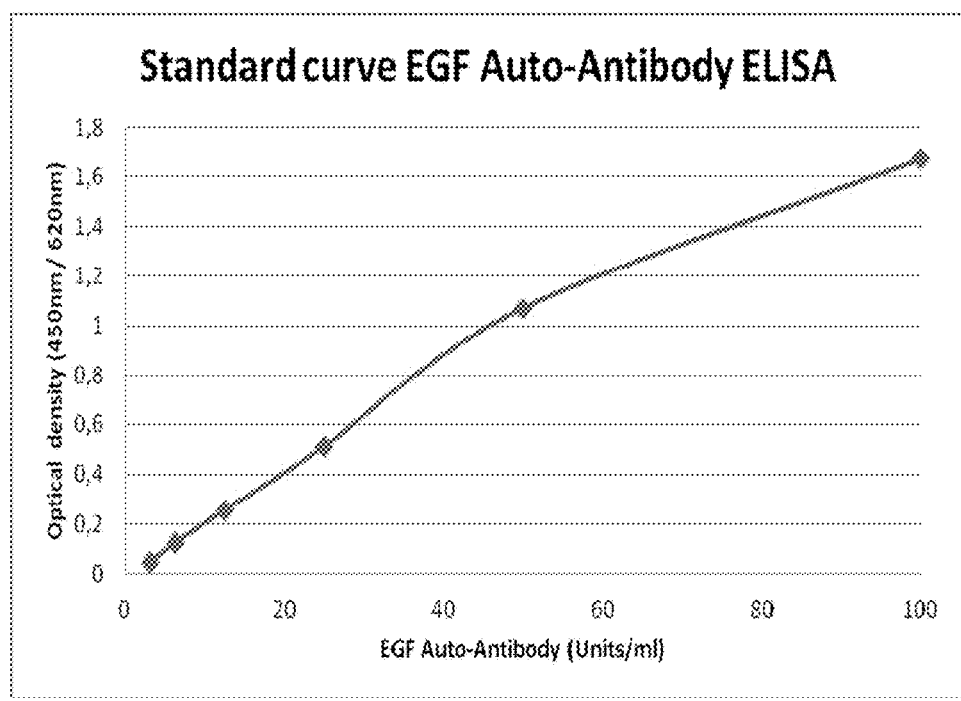
FIG. 6: Standard curve of the EGF-Auto-Antibody ELISA

As outlined herein, the levels of EGF antibodies in samples of the patient to be diagnosed and treated or to be treated are compared with the control groups as defined herein. However, in one embodiment the levels are compared to fixed values, i.e. thresholds under or over which a certain diagnosis, or prognosis of response is given. To this end, unit-standards may be applied. The present inventors set out such standard for the EGF using serum samples from systemic sclerosis patients. Systemic sclerosis patients are known to have high levels of autoimmune antibodies in general. Hence, the inventors took a serum sample of a systemic sclerosis patient. However, it will be acknowledged by the skilled person that also other samples may be taken to set a different standard, e.g. samples of healthy subjects, samples of cancer patients. Nevertheless the principle of generating a standard (units) is the same in any case and are exemplified herein using serum samples of systemic sclerosis patients. In the context of the present invention "units/ml", unless specified otherwise, refers to the concentration of antibodies standardised as exemplified herein. Hence, in one embodiment of the present invention 100 units/ml refers to a dilution of 1:400 of a serum sample of systemic sclerosis patients. The serum sample may be derived from a single patient or of a cohort of a plurality of patients, e.g. a cohort of 200 patients suffering from systemic sclerosis. The present inventors found that the concentration of EGF antibodies in samples of systemic sclerosis do not differ by more than about 10%, showing such standard being reproducible. In one preferred embodiment the standard for the concentrations of the autoimmune antibodies is generated in the following way: a serum sample of a systemic sclerosis patient (or a larger cohort) is diluted (a) 1:400 for standard point 100 Units/ml, (b) 1:800 for standard point 50 Units/ml, (c) 1:1600 for standard point 25 Units/ml, (d) 1:3200 for standard point 12.5 Units/ml, (e) 1:6400 for standard point 6.25 Units/ml and (f) 1:12800 for standard point 3.13 Units/ml. These standards are then used for the immunoassay chosen, e.g. ELISA, and then correlated with the respective read-out value, e.g. for ELISA optical density at 450 nm/optical density at 620 nm. A typical standard curve of an EGF auto-antibody ELISA is shown in FIG. 6. Nevertheless, the skilled person will readily understand that it may also be possible to standardize the levels of EGF-autoantibodies using different samples, e.g. samples of healthy subjects or cancer patients.

"equal" level in context with the present invention means that the levels differ by not more than ±10%, preferably by not more than ±5%, more preferably by not more than ±2%. "Decreased" or "increased" level in the context of the present invention mean that the levels differ by more than 10%, preferably by more than 15%, preferably more than 20%.

"Plasma" in the context of the present invention is the virtually cell-free supernatant of blood containing anticoagulant obtained after centrifugation. Exemplary anticoagulants include calcium ion binding compounds such as EDTA or citrate and thrombin inhibitors such as heparinates or hirudin. Cell-free plasma can be obtained by centrifugation of the anticoagulated blood (e.g. citrated, EDTA or heparinized blood) for at least 15 minutes at 2000 to 3000 g.

"Serum" is the liquid fraction of whole blood that is collected after the blood is allowed to clot. When coagulated blood (clotted blood) is centrifuged serum can be obtained as supernatant. It does not contain fibrinogen, although some clotting factors remain.

In the method of the present invention, the anti-EGF antibody is preferably detected in an immunoassay. Suitable immunoassays may be selected from the group of immunoprecipitation, enzyme immunoassay (EIA)), enzyme-linked immunosorbenassys (ELISA), radioimmunoassay (RIA), fluorescent immunoassay, a chemiluminescent assay, an agglutination assay, nephelometric assay, turbidimetric assay, a Western Blot, a competitive immunoassay, a non-competitive immunoassay, a homogeneous immunoassay a heterogeneous immunoassay, a bioassay and a reporter assay such as a luciferase assay. Preferably herein the immunoassay is an enzyme linked immunosorbent assay (ELISA), and luminex assays.

The immunoassays can be homogenous or heterogeneous assays, competitive and non-competitive assays. In a particularly preferred embodiment, the assay is in the form of a sandwich assay, which is a non-competitive immunoassay, wherein the anti-EGF antibody (i.e. the "analyte") to be detected and/or quantified is allowed to bind to an immobilized EGF protein or immunogenic peptide fragment thereof and to a secondary antibody. The EGF or fragment thereof (i.e. a peptide), may e.g., be bound to a solid phase, e.g. a bead, a surface of a well or other container, a chip or a strip, and the secondary antibody is an antibody which is labeled, e.g. with a dye, with a radioisotope, or a reactive or catalytically active moiety such as a peroxidase, e.g. horseradish peroxidase. The amount of labeled antibody bound to the analyte is then measured by an appropriate method. The general composition and procedures involved with "sandwich assays" are well-established and known to the skilled person (*The Immunoassay Handbook*, Ed. David Wild, Elsevier LTD, Oxford; 3rd ed. (May 2005), ISBN-13: 978-0080445267; Hultschig C et al., *Curr Opin Chem Biol.* 2006 February; 10(1):4-10. PMID: 16376134, incorporated herein by reference). Sandwich immunoassays can for example be designed as one-step assays or as two-step assays.

The detectable label may for example be based on fluorescence or chemiluminescence. The labelling system comprises rare earth cryptates or rare earth chelates in combination with a fluorescence dye or chemiluminescence dye, in particular a dye of the cyanine type. In the context of the present invention, fluorescence based assays comprise the use of dyes, which may for instance be selected from the group comprising FAM (5- or 6-carboxyfluorescein), VIC, NED, Fluorescein, Fluoresceinisothiocyanate (FITC), IRD-700/800, Cyanine dyes, such as CY3, CY5, CY3.5, CY5.5, Cy7, Xanthen, 6-Carboxy-2',4',7',4,7-hexachlorofluorescein (HEX), TET, 6-Carboxy-4',5'-dichloro-2',7'-dimethodyfluorescein (JOE), N,N,N',N'-Tetramethyl-6-carboxyrhodamine (TAMRA), 6-Carboxy-X-rhodamine (ROX), 5-Carboxyrhodamine-6G (R6G5), 6-carboxyrhodamine-6G (RG6), Rhodamine, Rhodamine Green, Rhodamine Red, Rhodamine 110, BODIPY dyes, such as BODIPY TMR, Oregon Green, Coumarines such as Umbelliferone, Benzimides, such as Hoechst 33258; Phenanthridines, such as Texas Red, Yakima Yellow, Alexa Fluor, PET, Ethidiumbromide, Acridinium dyes, Carbazol dyes, Phenoxazine dyes, Porphyrine dyes, Polymethin dyes, and the like.

In the context of the present invention, chemiluminescence based assays comprise the use of dyes, based on the physical principles described for chemiluminescent materials in Kirk-Othmer, *Encyclopedia of chemical technology*, 4$^{th}$ ed., executive editor, J. I. Kroschwitz; editor, M Howe-Grant, John Wiley & Sons, 1993, vol. 15, p. 518-562, incorporated herein by reference, including citations on pages 551-562. Preferred chemiluminescent dyes are acridiniumesters.

The "sensitivity" of an assay relates to the proportion of actual positives which are correctly identified as such, i.e. the ability to identify positive results (true positives positive results/number of positives). Hence, the lower the concentrations of the analyte that can be detected with an assay, the more sensitive the immunoassay is. The "specificity" of an assay relates to the proportion of negatives which are correctly identified as such, i.e. the ability to identify negative results (true negatives/negative results). For an antibody the "specificity" is defined as the ability of an individual antigen binding site to react with only one antigenic epitope. The binding behaviour of an antibody can also be characterized in terms of its "affinity" and its "avidity". The "affinity" of an antibody is a measure for the strength of the reaction between a single antigenic epitope and a single antigen binding site. The "avidity" of an antibody is a measure for the overall strength of binding between an antigen with many epitopes and multivalent antibodies.

An "immunogenic peptide" or "antigenic peptide" as used herein is a portion of an EGF protein that is recognized (i.e., specifically bound) by the anti-EGF antibody. Such immunogenic peptides generally comprise at least 5 amino acid residues, more preferably at least 10, and still more preferably at least 20 amino acid residues of EGF. However, they may also comprise at least 30, 40, 50, 60, 70, 80, 90, 100, 110, 120, 130, 140 or 150 amino acid residues. For example, a EGF polypeptide fragment corresponding to mature EGF peptide, e.g. residues 930 to 982 of SEQ ID NO: 1 can be used in the context of the methods and immunoassays of the present invention, preferably a peptide comprising the sequence of SEQ ID NO:2.

For the purposes of the immunoassays and diagnostic methods of the invention EGF by expression in cells, preferably eukaryotic cells or in cell free, preferably eukaryotic cell free systems. Hence, in the assays and methods of the invention EGF may be present in its natural cellular environment and can be used together with the material associated with the factor in its natural state as well as in isolated form. Suitable expression systems include Chinese hamster ovary (CHO) cells overexpressing the human EGF. Hence, cell extracts (particularly extracts from CHO cells overexpressing the human EGF) can be used to detect anti-EGF antibodies. Based on the weight of the whole receptor in the preparation (e.g. the "extract") to be used according to the invention, the isolated receptor should account for at least 0.5%, preferably at least 5% more preferably at least 25%, and in a particular preferred embodiment at least 50%. The receptor is preferably used in isolated form, i.e. essentially free of other proteins, lipids, carbohydrates or other substances naturally associated with the receptor. "Essentially free of" means that the receptor is at least 75%, preferably at least 85%, more preferably at least 95% and especially preferably at least 99% free of other proteins, lipids, carbohydrates or other substances naturally associated with the factor.

In particular, the method of the present invention comprises the steps of
(a) contacting the sample with EGF or an antigenic peptide fragment under conditions allowing for the formation of a complex between anti-EGF antibodies with EGF or the antigenic peptide fragment thereof,
(b) detecting the complex.

Hence, the invention relates to an immunoassay method for detecting an anti-EGF antibody in a sample from a subject, comprising the steps of
(a) contacting the sample suspected of comprising an anti-EGF antibody with EGF or an antigenic peptide fragment thereof under conditions allowing for the formation of a complex between the anti-EGF antibody with EGF or the antigenic peptide fragment thereof,
(b) detecting the complex.

The EGF or the antigenic peptide fragment thereof may preferably be immobilized on a surface. The complex may for example be detected using a secondary antibody against the Fc portion of the anti-EGF antibody. When the anti-EGF antibody is an IgG-antibody, the secondary antibody may be an anti-IgG antibody. In a particular embodiment, the subject is a human and
(i) the anti-EGF antibody is a IgG1-antibody and the secondary antibody is an anti-human-IgG1 antibody; or
(ii) the anti-EGF antibody is a IgG2-antibody and the secondary antibody is an anti-human-IgG2 antibody; or
(iii) the anti-EGF antibody is a IgG3-antibody and the secondary antibody is an anti-human-IgG3 antibody; or
(iv) the anti-EGF antibody is a IgG4-antibody and the secondary antibody is an anti-human-IgG4 antibody.

The secondary antibody may for example be labeled with a detectable marker, e.g. a peroxidase.

Furthermore, in the methods of the present invention further parameters of the subject may be considered as well for diagnosis, differential diagnosis, prognosis of response etc. Such parameters in a multivariate model may include gender, age, histological evaluation, Figo or histopathological staging, grading of the tumor and other markers. Dependent variables for determining survival may also be time till death, time till first relapse, time till death or first relapse (shorter interval if both events occurred). A Cox-Proportional-Hazard regression predicts the dependent variable based on one or more independent variables. These predictors can either be measures (as e.g. level of a biomarker) or categorical data (as e.g. response to a previous treatment). The skilled person is aware of the fact that diagnostic markers only give a certain degree of sensitivity and specificity, as also outlined herein. He knows that different further parameters might be considered in order to increase both. For example, when detecting levels of a marker indicative for epithelial cancer, inter alia ovarian cancer, the skilled person would not diagnose ovarian cancer in a male human subject. Nevertheless, the present invention provides a new and superior marker for diagnosis, prognosis of cancer, particularly for ovarian cancer. In the context of the methods of the invention and particularly the immunoassays of the invention, the presence of one or more further diagnostic markers for ovarian cancer is detected in the sample. For example, in a diagnostic method of the present invention levels of CA125, Human Epidymis Protein 4 (HE4) and/or Mesothelin are detected in addition.

The invention also relates to the use of EGF or an antigenic peptide fragment thereof, preferably as set out herein above, for the diagnosis of cancer, preferably for the diagnosis of an epithelial cancer, more preferably for the diagnosis of a cancer selected from the group consisting of ovarian cancer, lung cancer, renal cancer, gastric cancer, liver cancer, pancreatic cancer, prostate cancer, colon cancer, and colorectal cancer.

In the context of the present invention, the levels of the anti-EGF antibodies a may be analyzed in a number of fashions well known to a person skilled in the art. For example, each assay result obtained may be compared to a "normal" value, or a value indicating a particular disease or outcome. A particular diagnosis/prognosis may depend upon the comparison of each assay result to such a value, which may be referred to as a diagnostic or prognostic "threshold". In certain embodiments, assays for one or more diagnostic or prognostic indicators are correlated to a condition or disease by merely the presence or absence of the indicator(s) in the assay. For example, an assay can be designed so that a positive signal only occurs above a particular threshold concentration of interest, and below which concentration the assay provides no signal above background.

The sensitivity and specificity of a diagnostic and/or prognostic test depends on more than just the analytical "quality" of the test, they also depend on the definition of what constitutes an abnormal result. In practice, Receiver Operating Characteristic curves (ROC curves), are typically calculated by plotting the value of a variable versus its relative frequency in "normal" (i.e. apparently healthy individuals not having ovarian cancer) and "disease" populations. For any particular marker, a distribution of marker levels for subjects with and without a disease will likely overlap. Under such conditions, a test does not absolutely distinguish normal from disease with 100% accuracy, and the area of overlap indicates where the test cannot distinguish normal from disease. A threshold is selected, below which the test is considered to be abnormal and above which the test is considered to be normal. The area under the ROC curve is a measure of the probability that the perceived measurement will allow correct identification of a condition. ROC curves can be used even when test results don't necessarily give an accurate number. As long as one can rank results, one can create a ROC curve. For example, results of a test on "disease" samples might be ranked according to degree (e.g. 1=low, 2=normal, and 3=high). This ranking can be correlated to results in the "normal" population, and a ROC curve created. These methods are well known in the art. See, e.g., Hanley et al. 1982. *Radiology* 143: 29-36. Preferably, a threshold is selected to provide a ROC curve area of greater than about 0.5, more preferably greater than about 0.7, still more preferably greater than about 0.8, even more preferably greater than about 0.85, and most preferably greater than about 0.9. The term "about" in this context refers to +/−5% of a given measurement.

The horizontal axis of the ROC curve represents (1-specificity), which increases with the rate of false positives. The vertical axis of the curve represents sensitivity, which increases with the rate of true positives. Thus, for a particular cut-off selected, the value of (1-specificity) may be determined, and a corresponding sensitivity may be obtained. The area under the ROC curve is a measure of the probability that the measured marker level will allow correct identification of a disease or condition. Thus, the area under the ROC curve can be used to determine the effectiveness of the test.

In other embodiments, a positive likelihood ratio, negative likelihood ratio, odds ratio, or hazard ratio is used as a measure of a test's ability to predict risk or diagnose a disease. In the case of a positive likelihood ratio, a value of 1 indicates that a positive result is equally likely among subjects in both the "diseased" and "control" groups; a value greater than 1 indicates that a positive result is more likely in the diseased group; and a value less than 1 indicates that a positive result is more likely in the control group. In the case of a negative likelihood ratio, a value of 1 indicates that a negative result is equally likely among subjects in both the "diseased" and "control" groups; a value greater than 1 indicates that a negative result is more likely in the test group; and a value less than 1 indicates that a negative result is more likely in the control group.

In the case of an odds ratio, a value of 1 indicates that a positive result is equally likely among subjects in both the "diseased" and "control" groups; a value greater than 1 indicates that a positive result is more likely in the diseased group; and a value less than 1 indicates that a positive result is more likely in the control group.

In the case of a hazard ratio, a value of 1 indicates that the relative risk of an endpoint (e.g., death) is equal in both the "diseased" and "control" groups; a value greater than 1 indicates that the risk is greater in the diseased group; and a value less than 1 indicates that the risk is greater in the control group.

The skilled artisan will understand that associating a diagnostic or prognostic indicator, with a diagnosis or with a prognostic risk of a future clinical outcome is a statistical analysis. For example, a marker level of lower than X may signal that a patient is more likely to suffer from an adverse outcome than patients with a level more than or equal to X, as determined by a level of statistical significance. Additionally, a change in marker concentration from baseline levels may be reflective of patient prognosis, and the degree of change in marker level may be related to the severity of adverse events. Statistical significance is often determined by comparing two or more populations, and determining a confidence interval and/or a p value. See, e.g., Dowdy and Wearden, *Statistics for Research*, John Wiley & Sons, New York, 1983. Preferred confidence intervals of the invention are 90%, 95%, 97.5%, 98%, 99%, 99.5%, 99.9% and 99.99%, while preferred p values are 0.1, 0.05, 0.025, 0.02, 0.01, 0.005, 0.001, and 0.0001.

Suitable threshold levels for the stratification of subjects into different groups (categories) have to be determined for each particular combination of EGF-antibodies, disease and/or medication. This can e.g. be done by grouping a reference population of patients according to their level of EGF-antibodies into certain quantiles, e.g. quartiles, quintiles or even according to suitable percentiles. For each of the quantiles or groups above and below certain percentiles, hazard ratios can be calculated comparing the risk for an adverse outcome, i.e. an "cancer" or a "non response", e.g. in terms of survival rate/mortality, between those patients who have received a certain medication and those who did not, or in terms of presence and absence of cancer in patients. In such a scenario, a hazard ratio (HR) above 1 indicates a higher risk for an adverse outcome for the patients who have received a treatment than for patients who did not. A HR below 1 indicates beneficial effects of a certain treatment in the group of patients. A HR around 1 (e.g. +/−0.1) indicates no elevated risk but also no benefit from medication for the particular group of patients. By comparison of the HR between certain quantiles of patients with each other and with the HR of the overall population of patients, it is possible to identify those quantiles of patients who have an elevated risk and those who benefit from medication and thereby stratify subjects according to the present invention.

In some cases presence of cancer, relapse and/or mortality upon treatment with an angiogenesis inhibitor will affect patients with high levels (e.g. in the fifth quintile) of EGF-antibodies, while in other cases only patients with low levels of EGF-antibodies will be affected (e.g. in the first quintile). However, with the above explanations, a skilled person is able to identify those groups of patients having cancer, those groups that do respond to a medication and those groups that do not respond to the medication. Exemplarily, some combinations of hormones and medications are listed for several diseases in the appended examples. In another embodiment of the invention, the diagnosis, risk for relapse of cancer and/or mortality and/or outcome for a patient are determined by relating the patient's individual level of marker peptide to certain percentiles (e.g. $97.5^{th}$ percentile) of a healthy population.

Kaplan-Meier estimators may be used for the assessment or prediction of the outcome or risk (e.g. diagnosis, relapse, progression or morbidity) of a patient.

The invention also pertains to a research and/or diagnostic kit for the diagnosis of cancer, e.g. ovarian cancer, or for the prediction of risk stratification for relapse of cancer and/or mortality in a patient, wherein the kit comprises EGF or an antigenic peptide fragment thereof. The kit may further comprise an antibody directed to the Fc portion of the anti-EGF antibody to be detected, i.e. an anti-human IgG antibody.

Such kits can comprise a carrier, package or container that is compartmentalized to receive one or more containers such as vials, tubes, and the like, each of the container(s) comprising one of the separate elements to be used in the method. The kit of the invention will typically comprise the container described above and one or more other containers comprising materials desirable from a commercial and user standpoint, including buffers, diluents, filters, needles, syringes, and package inserts with instructions for use. In addition, a label can be provided on the container to indicate that the composition is used for a specific therapeutic or non-therapeutic application, and can also indicate directions for either in vivo or in vitro use, such as those described herein. Directions and or other information can also be included on an insert which is included with the kit.

The term "drug" in connection with the present invention is to be understood as any substance, pharmaceutical composition or the like which are intended for the treatment of cancer, preferably an epithelial cancer as outlined herein, particularly preferred ovarian cancer. Different drugs are known. Drugs used in the treatment of cancer include therapeutic antibodies such as panitumumab, cetuximab, zalutumumab, nimotuzumab, and matuzumab, and are preferably selected from this group The inventors found response of patients suffering from cancer to a drug inhibiting EGFR activity, e.g. panitumumab, may be predicted by determining the levels of EGF antibodies in samples from a patient to be treated. Panitumumab (INN), formerly ABX-EGF, is a fully human monoclonal antibody specific to the epidermal growth factor receptor (also known as EGF receptor, EGFR, ErbB-1 and HER1 in humans). Panitumumab is manufactured by Amgen and marketed as Vectibix. It was originally developed by Abgenix Inc. Panitumumab works by binding to the extracellular domain of the EGFR preventing its activation. This results in halting of the cascade of intracellular signals dependent on this receptor (Plunkett, Jack W. (Sep. 30, 2005). Plunkett's Biotech & Genetics Industry Almanac 2006. Plunkett Research, Ltd. ISBN 1-59392-033-4). In a preferred embodiment the drug used for the treatment of cancer are drugs directed against EGFR, e.g. antibodies binding EGFR, preferably at the extracellular part, and inhibitors of EGFR activity, e.g. by inhibiting the binding EGF to its receptor or by inhibiting the kinase activity of EGFR. Such inhibitors are known and include panitumumab, gefitinib, erlotinib, cetuximab, lapatinib, vandetanib, trastuzumab, zalutumumab, nimotuzumab, and matuzumab, which are preferred drugs in connection with the present invention, particularly preferred is panitumumab. Furthermore, "drug" also refers to chemotherapeutic agents. Preferred chemotherapeutic agents are platinum analogues used for treating cancer. Such platinum analogues are known by the skilled person and are preferably selected form the group consisting of cisplatin, carboplatin, oxaliplatin, satraplatin, and triplatin-tetranitrate, preferably cisplatin or carboplatin.

The skilled person is able to determine whether a substance or drug is an "inhibitor of EGFR activity". He may apply different approaches to test whether a substance, when applied to the EGFR inhibits its function. The skilled person may test whether the formation of dimmers of EGFR is inhibited if the substance or drug is present. It may also be tested whether the activation of downstream components of EGFR, e.g. downstream signaling proteins, is inhibited. Usually activation occurs if for example EGF is bound to the EGFR. One might test whether downstream signal transduction cascades, principally the MAPK, Akt and JNK pathways, leading to DNA synthesis and cell proliferation, are activated or not if the substance or drug to be tested in present in addition. Different methods and approaches may be applied to this end and include in vivo and in vitro assays.

Also encompassed by the invention is a method of treating cancer in a subject, comprising determining the level of antibodies against EGF in a sample from the subject, wherein when the level of anti-EGF antibodies in a sample from the subject is above 60 units/ml, a drug is administered to the subject, preferably at levels above 65 units/ml, further preferred above 70 units/ml, also preferred at levels above 80 units/ml, a drug as defined herein is administered to the subject. Preferably the invention encompasses a method of treating ovarian cancer in a subject, comprising determining the level of antibodies against EGF in a sample from the subject, wherein when the level of anti-EGF antibodies in a sample from the subject is above 60 units/ml, a drug is administered to the subject, preferably at levels above 65 units/ml, further preferred above 70 units/ml, also preferred at levels above 80 units/ml, a drug as defined herein is administered to the subject. Drugs used in the treatment of cancer include compounds or antibodies inhibiting EGFR activity, such as panitumumab gefitinib, erlotinib, cetuximab, lapatinib, vandetanib, trastuzumab, zalutumumab, nimotuzumab, and matuzumab.

The invention, thus, also relates a drug for use in the treatment of cancer in a subject, wherein the drug is administered to the subject when the level anti-EGF antibodies in a sample from the subject is above 60 units/ml, preferably at levels above 65 units/ml, further preferred above 70 units/ml, also preferred at levels above 80 units/ml. In a preferred embodiment the drug is for use in the treatment of an epithelial cancer, preferably selected from the group consisting of ovarian cancer, lung cancer, renal cancer, gastric cancer, liver cancer, pancreatic cancer, prostate cancer, colon cancer, and colorectal cancer. The drug is preferably selected from the group consisting of panitumumab, gefitinib, erlotinib, cetuximab, lapatinib, vandetanib, trastuzumab, zalutumumab, nimotuzumab, and matuzumab. In a further preferred embodiment the drug is an EGFR inhibitor, preferably for use in the treatment of ovarian cancer, more preferably a monoclonal antibody binding EGFR, preferably binding the extracellular part of EGFR, preferably selected from the group consisting of panitumumab, gefitinib, erlotinib, cetuximab, lapatinib, vandetanib, trastuzumab, zalutumumab, nimotuzumab, and matuzumab. The drug in a particular preferred embodiment is panitumumab. The invention, thus, also relates to panitumumab for use in the treatment of ovarian cancer in a subject, wherein panitumumab is administered to the subject when the level anti-EGF antibodies in a sample from the subject is above 60 units/ml, preferably at levels above 65 units/ml, further preferred above 70 units/ml, also preferred at levels above 80 units/ml.

The invention furthermore relates to a (diagnostic) kit for diagnosing cancer, or predicting the response of a cancer patient to the treatment of an EGFR inhibitor, said kit comprising EGF or an antigenic peptide thereof, and means to detect antibodies binding to said EGF or peptide thereof. Preferably the kit is designed for a method of the present invention. It will be understood that the embodiments disclosed herein above for EGF or an antigenic peptide thereof as set out herein above also apply to the kit. The kit is designed to detect autoimmune antibodies in samples of subject and hence comprises means to detect such antibodies, particularly antibodies binding to said EGF or peptide thereof. Such means are outlined herein above, e.g. for immunoassays. The embodiments set out for the immunoassays apply also to the kit of the invention. The kits of the present invention are meant for the detection of autoimmune antibodies. Hence, in one embodiment they comprise means for the preparation of blood, e.g. for gaining serum thereof. Furthermore, the kit may comprise control composition and/or standards. The control composition preferably comprises EGF antibodies as positive control. Furthermore, the kit may comprise one or a plurality of standard compositions. A standard composition comprises EGF antibodies at a defined concentration.

As outlined herein, determination of concentration of autoimmune-antibodies may be performed using standard curves. These curves set out which concentration of antibodies in a sample or solution corresponds to what read-out value of the assay used, e.g. optical density or proportion of optical density at different wavelengths (e.g. 450 nm/620 nm). To this end the kits of the present invention may comprise one or more standard compositions having a defined concentration of EGF antibodies, preferably of the kind to be detected in the method. A standard composition of the kits according to the present invention comprise EGF antibodies at concentrations selected from the group consisting of 100 units/ml, 50 units/ml, 25 units/ml, 12.5 units/ml, 6.25 units/ml, and 3.13 units/ml. In one embodiment the kit comprises six standard compositions with the recited concentration. In another embodiment the kit comprises one standard composition with the highest concentration of the standard curve, e.g. 200 units/ml or 100 units/ml. The other concentrations may be produced at the side of the end user by further dilutions, e.g. in PBS. A dilution buffer may therefore also be comprised in the kits according to the invention.

It will be readily understood that the embodiments outlined above shall apply to the invention as a whole and not be limited to a specific method, unless stated otherwise. It will for example be understood the embodiments for the type of cancer shall be applied to every method, kit or the like disclosed herein. The invention is further illustrated by the following non-limiting examples and Figures.

Sequences

Amino acid sequence of the human EGF [SEQ ID NO: 1]:

| | |
|---|---|
| 1 | MLLTLIILLP VVSKFSFVSL SAPQHWSCPE GTLAGNGNST CVGPAPFLIF |
| 51 | SHGNSIFRID TEGTNYEQLV VDAGVSVIMD FHYNEKRIYW VDLERQLLQR |
| 101 | VFLNGSRQER VCNIEKNVSG MAINWINEEV IWSNQQEGII TVTDMKGNNS |
| 151 | HILLSALKYP ANVAVDPVER FIFWSSEVAG SLYRADLDCV CVKALLETSE |
| 201 | KITAVSLDVL DKRLFWIQYN REGSNSLICS CDYDGCSVHI SKEPTQHNLF |
| 251 | AMSLECDRIF YSTWKMKTIW IANKHTGKDM VRINLHSSFV PLCELKVVHP |
| 301 | LAQPKAEDDT WEPEQKLCKL RKGNCSSTVC GQDLQSHLCM CAECYALSRD |
| 351 | RKYCEDVNEC AFWNHGCTLG CKNTPGSYYC TCPVCFVLLP DGKRCHQLVS |
| 401 | CPRNVSECSH DCVLTSEGPL CFCPEGSVLE RDGKTCSCCS SPDNGGCSQL |

-continued

| | | Sequences | | |
|---|---|---|---|---|
| 451 | CVPLSPVSWE | CDCFPGYDLQ | LDEKSCAASG | PQPFLLFANS | QDIRHMHEDG |
| 501 | TDYGTLLSQQ | MGMVYALDHD | PVENKIYFAH | TALKWIERAN | MDGSQRERLI |
| 551 | EEGVDVPEGL | AVDWIGRRFY | WTDRGKSLIG | RSDLNGKRSK | IITKENISQP |
| 601 | RGIAVHPMAK | RLFWTDTGIN | PRIESSSLQC | LCRLVIASSD | LIWPSGITID |
| 651 | FLTDKLYWCD | AKQSVIEMAN | LDGSKRRRLT | QNDVCHPFAV | AVFEDYVWFS |
| 701 | DWAMPSVMRV | NKRTGKDRVR | LQGSMLKPSS | LVVYHPLAKP | GADPCLYQNG |
| 751 | GCEHICKKRL | GTAWCSCREG | FMKASDGKTC | LALDCHQLLA | CGEVDLKNQV |
| 801 | TPLDILSKTR | VSEDNITESQ | HMLVAEIMVS | DQDDCAPVGC | SMYARCISEG |
| 851 | EDATCQCLKG | FAGDGKLCSD | IDECEMGVPV | CPPASSKCIN | TEGGYVCRCS |
| 901 | EGYQCDCIHC | LDSTPPPHLR | EDDHHYSVRN | SDSECPLSHD | GYCLHDGVCM |
| 951 | YIEALDKYAC | NCVVGYIGER | CQYRDLKWWE | LRHACHCQQQ | KVIVVAVCVV |
| 1001 | VLVMLLLLSL | WGAHYYRTQK | LLSKNPKNPY | EESSRDVRSR | RPADTEDGMS |
| 1051 | SCPQPWFVVI | KEHQDLKNGG | QPVACEDGQA | ADCSMQPTSW | RQEPQLCGMG |
| 1101 | TEQGCWIPVS | SDKGSCPQVM | ERSEHMPSYC | TQTLEGGVEK | PHSLLSANPL |
| 1151 | WQQRALDPPH | QMELTQ | | | |

Amino acid sequence of the human mature EGF peptide [SEQ ID NO: 2]
[amino acids 930 to 982 of SEQ ID NO: 1]:
```
   1    NSDSECPLSH DGYCLHDGVC MYIEALDKYA CNCVVGYIGE RCQYRDLKWW
  51    ELR
```

EXAMPLES

Example 1

We measured the anti-EGF autoantibody in serum samples using a sandwich ELISA kit (CellTrend GmbH Luckenwalde, Germany). The microtiter 96-well polystyrene plates were coated with recombinant human mature EGF of SEQ ID NO:2 expressed in *Escherichia coli*. To maintain the conformational epitopes of the receptor, 1 mM calcium chloride was added to every buffer. Duplicate samples of a 1:100 serum dilution were incubated at 4° C. for 2 hours. After washing steps, plates were incubated for 60 minutes with a 1:20.000 dilution of horseradish-peroxidase-labeled goat anti-human IgG (Jackson, USA) used for detection. In order to obtain a standard curve, plates were incubated with test sera from an anti-EGF autoantibody positive index patient. The ELISA was validated according to the FDA's "Guidance for industry: Bioanalytical method validation".

EGF-Auto-Antibodies are not available; a serum sample from a patient with a systemic sclerosis is used for the standard curve. A 1:400 dilution of the serum sample was defined as 100 units/ml EGF-Antibodies. A 1:100 dilution of a serum sample of a healthy control served as a positive control (range 20.0-30.0 units/ml). To set a standard for the concentrations of the autoimmune antibodies, a standard curve was generated. In detail, a serum sample of a systemic sclerosis patient was diluted (a) 1:400 for standard point 100 Units/ml, (b) 1:800 for standard point 50 Units/ml, (c) 1:1600 for standard point 25 Units/ml, (d) 1:3200 for standard point 12.5 Units/ml, (e) 1:6400 for standard point 6.25 Units/ml and (f) 1:12800 for standard point 3.13 Units/ml. Then the optical density was determined using the kit and method of example 1. Each standard point was performed in duplicates. Results are shown in FIG. 6.

Example 2

Anti-EGF antibody levels in serum samples from 132 healthy donors ("Control") and 201 patients with ovarian cancer ("OvCA") were measured using the kit and method of example 1. The levels were determined in units/mL. FIG. 1 shows the mean values of the natural logarithm of the EGF antibody level for OvCA and Control subjects. Patient suffering from ovarian cancer had significantly lower levels ($p<0.0001$) of anti-EGF antibodies as compared to healthy controls.

Example 3

Figure 2:
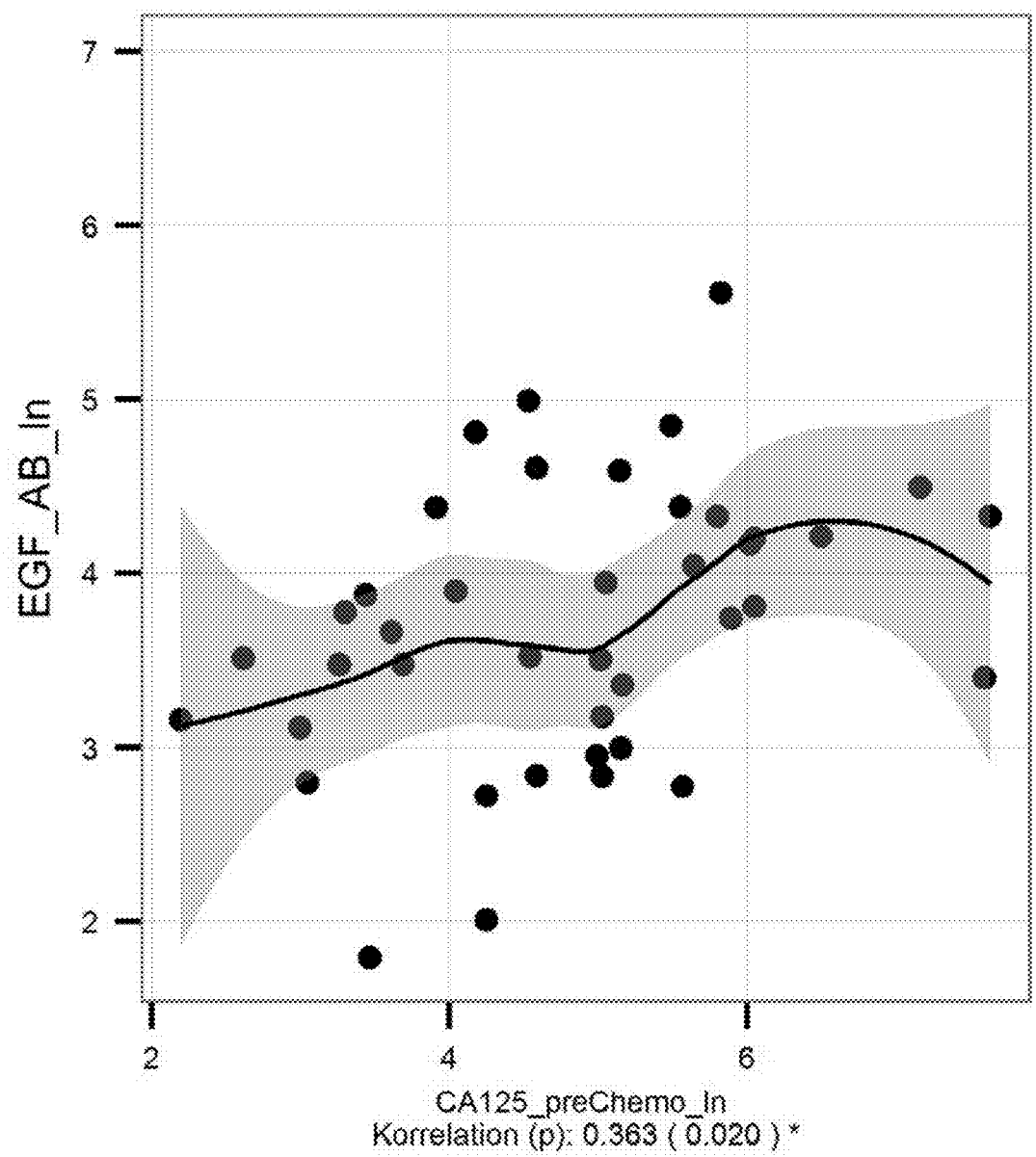
FIG. 2: A: Correlation of ln of mean levels of anti-EGF antibodies (ln of units/ml) and CA 125 level [units/ml; determined with commercially available kits] in serum/samples of ovarian cancer patients before onset of chemotherapy. B: Correlation of the decrease in levels of anti-EGF antibodies and CA 125 levels from before chemotherapy to before surgical removal.
Figure 2:
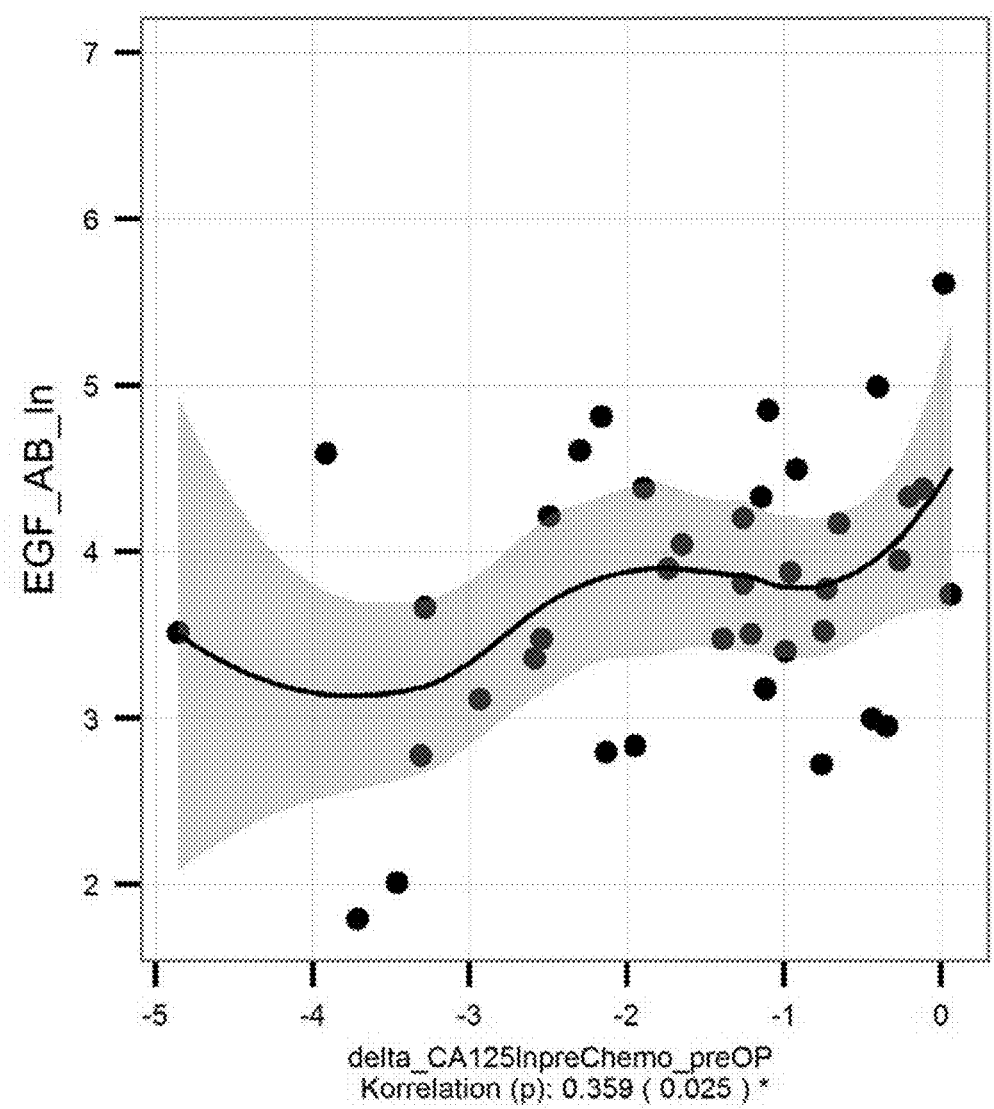

Levels of EGF antibodies in samples from patients suffering from ovarian cancer were determined before onset of surgical removal of the cancer. The patients were treated with a chemotherapeutic agent (platinum analogue) after surgical removal of ovarian cancer. A second sample was taken from each patient after surgical treatment and before onset of chemotherapeutic treatment. EGF antibody level was determined in all samples and correlated to respective CA125 levels in the same samples. Results are given in FIG. 2. Before chemotherapy was started a significant positive correlation could be observed between CA125 levels an levels of anti-EGF antibodies (FIG. 2A): correlation: 0.363 ($p=0.02$). The same significance is present when comparing amount of Ca125 decrease (delta) from before-Chemotherapy to before operation and the respective decrease in levels of anti-EGF antibodies (FIG. 2B): correlation: 0.359 (p=0.025).

Example 4

Figure 5:
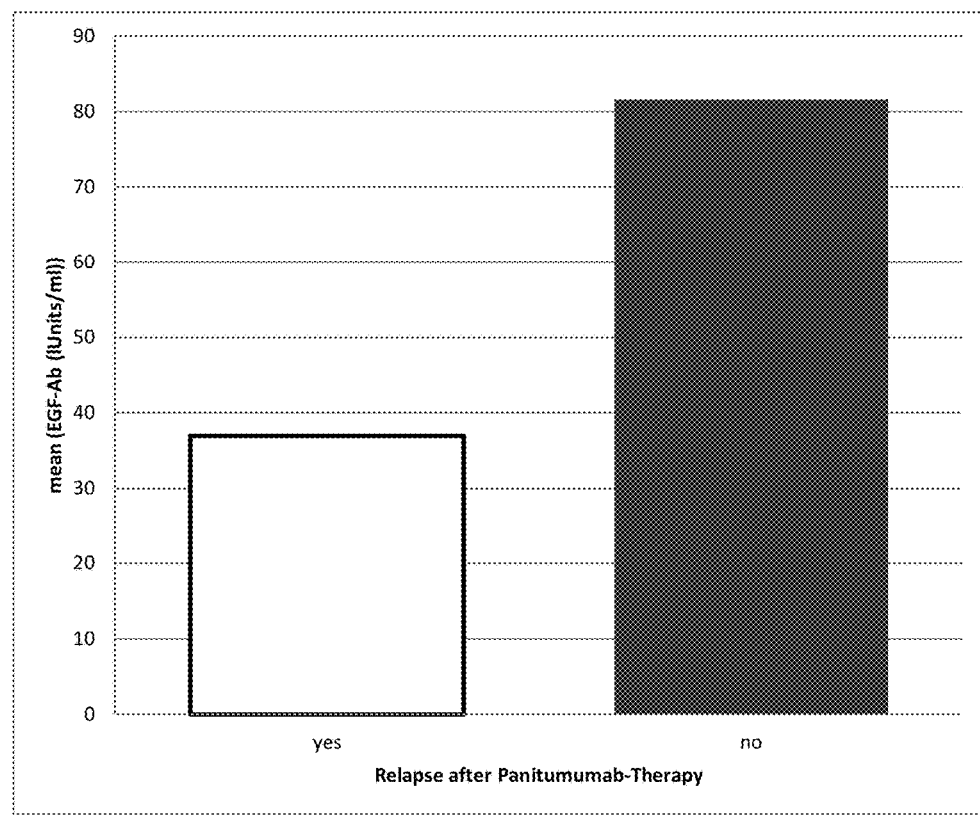
FIG. 5: Prediction of relapse after treatment of ovarian cancer with panitumumab. Samples were taken before onset of treatment. Levels of antibodies dieected against EGF were measured. The patients were categorized as "relapse" or "no relapse" and showed a EGF antibody level of 37.0 units/ml or 81.6 units/ml (mean values), respectively.

Levels of the EGF-antibody were compared in patients showing relapse of ovarian cancer after therapy with panitumumab and patients showing no relapse. Treatment was conducted and monitored by physicians. Samples of patients were taken before treatment. Patients were categorized as "relapse" or "no relapse" according to the reoccurrence of cancer after a period of 6 months. Levels of EGF-antibody were determined as outlined in Example 1. The results are shown in FIG. 5. Levels of EGF antibodies were higher in patients who had no relapse, compared to patients who had a relapse.

Example 5

Figure 3:
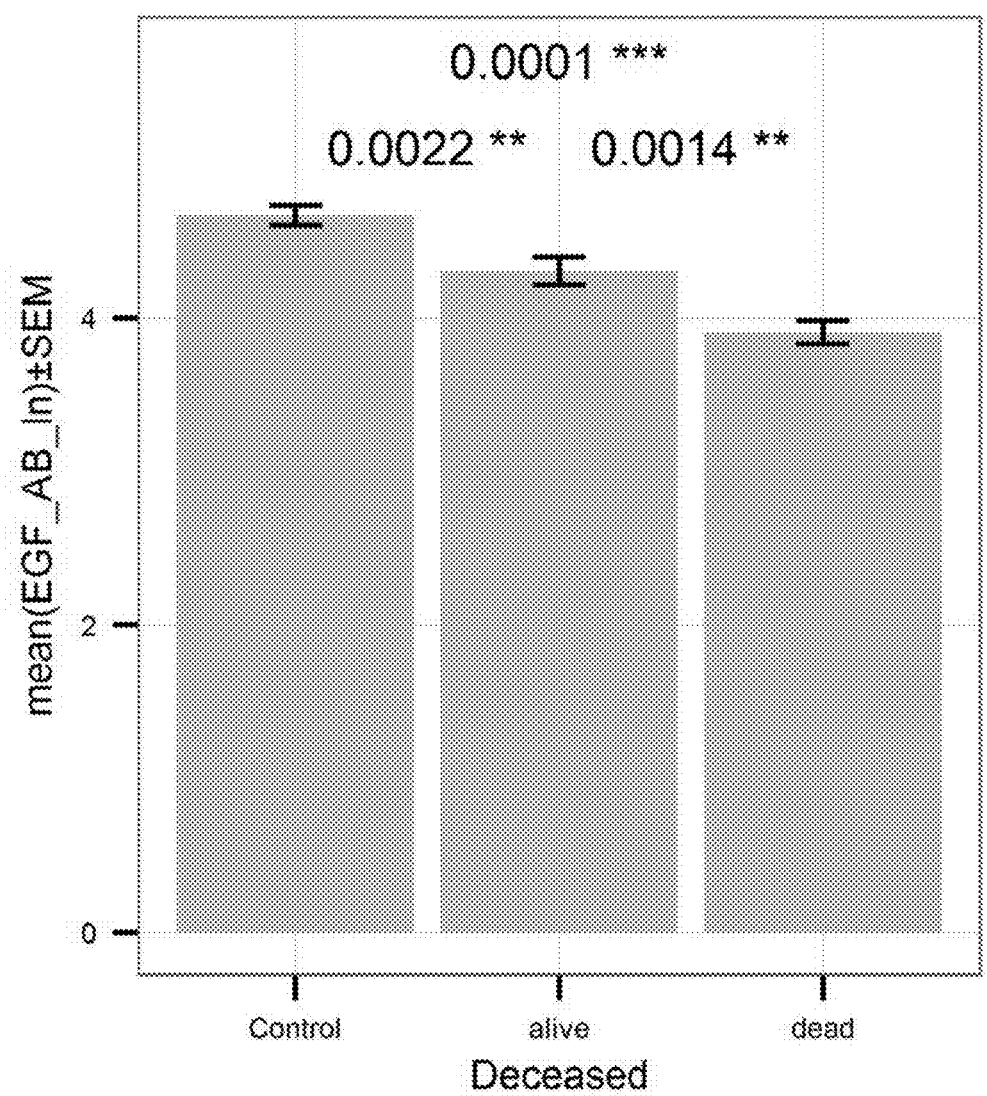
FIG. 3: Comparison of the ln of mean level of anti-EGF antibodies (ln of units/ml) in serum samples of ovarian cancer patients who survived after panitumumab treatment ("alive"; ln of mean=4.301; n=71) to the ln of mean level of anti-EGF antibodies in serum samples of ovarian cancer patients who died after treatment with panitumumab ("dead"; ln of mean=3.903 units/ml; n=128). The left column gives the healthy control group. P-values are indicated above (0.0022 between "control" and "alive", 0.0001 between "control" and "dead", and 0.0014 between "alive" and "dead"). Bars indicate standard error of mean.

Serum samples of ovarian cancer patients were taken before treatment with a platinum analogue after surgical removal of the tumor. The treatment was conducted by physicians. The patients were categorized into survivors ("alive") and patients who died after treatment with a platinum analogue ("dead"). The levels of anti-EGF antibodies were determined as outlined in Example 1. The results are shown in FIG. 3. Levels of anti-EGF antibodies were lower in patients of the "dead" group (ln of mean: 4.301 units/ml) compared to the "survival" group (ln of mean: 3.903 units/ml), the different was significant (p=0.0014).

Example 6

Figure 4:
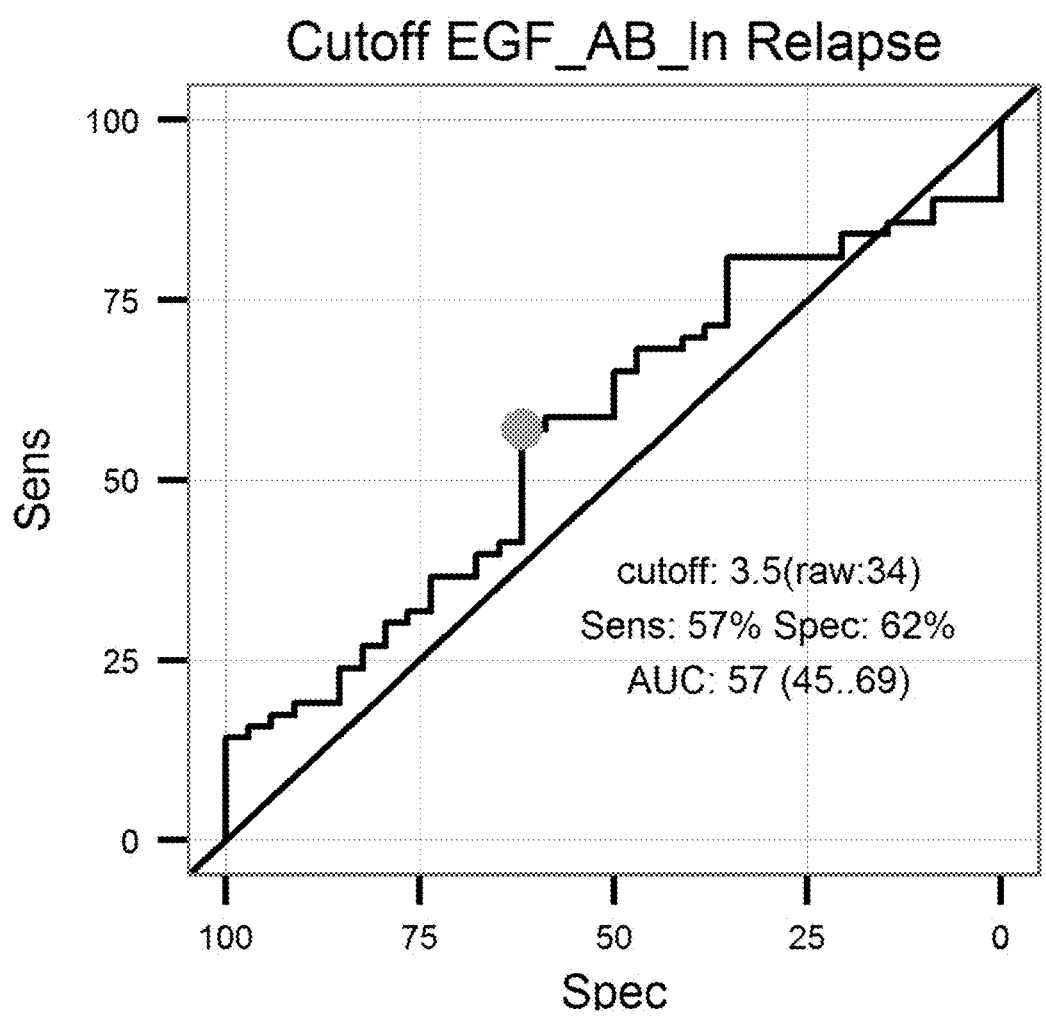
FIG. 4: A: on top sensitivity of the prediction of relapse of ovarian cancer after surgical removal of the tumor and subsequent treatment with an platinum analogue is plotted against the specificity. Ln of the Cutoff value (3.5 units/ml) and AUC is given in the graph. Below the proportion of patients not showing relapse after surgical removal of the tumor and subsequent treatment with an platinum analogue is shown over the time for patients having antibody levels below the ROC-cutoff value (dotted line) and above the ROC-cutoff value (solid line). B: on top sensitivity of the prediction of survival after surgical removal of the tumor and subsequent treatment with an platinum analogue is plotted against the specificity. Ln of the Cutoff value (3.4 units/ml) and AUC is given in the graph. Below the proportion of patients surviving after surgical removal of the tumor and subsequent treatment with an platinum analogue is shown over the time for patients having antibody levels below the ROC-cutoff value (dotted line) and above the ROC-cutoff value (solid line). C: on the left sensitivity of the prediction of a combined endpoint (death or relapse of cancer) of ovarian cancer patients after surgical removal of the tumor and subsequent treatment with an platinum analogue is plotted against the specificity. Ln of the Cutoff value (3.6 units/ml) and AUC is given in the graph. Below the proportion of patients surviving or not showing relapse of cancer after surgical removal of the tumor and subsequent treatment with an platinum analogue is shown over the time for patients having antibody levels below the ROC-cutoff value (dotted line) and above the ROC-cutoff value (solid line).
Figure 4:
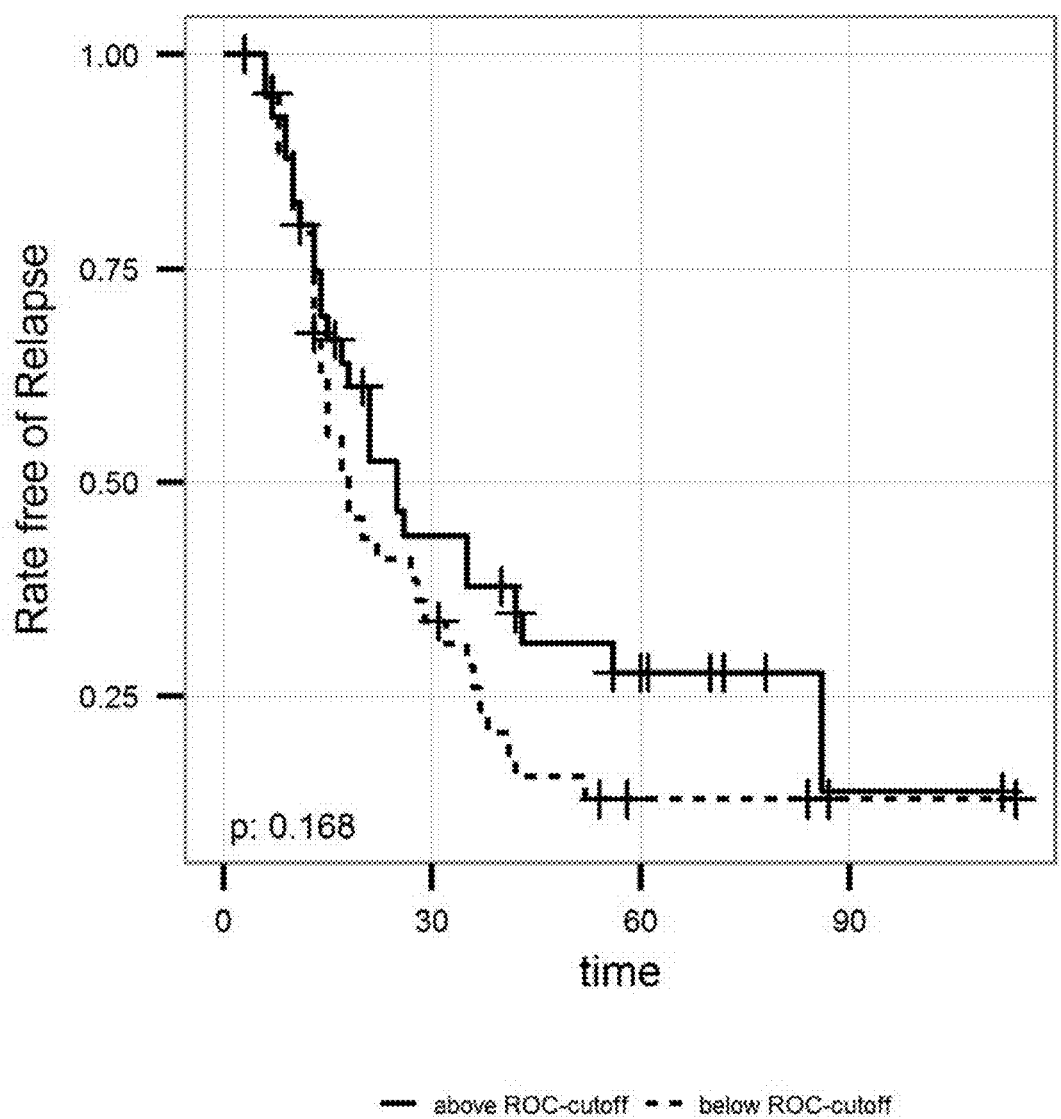
Figure 4:
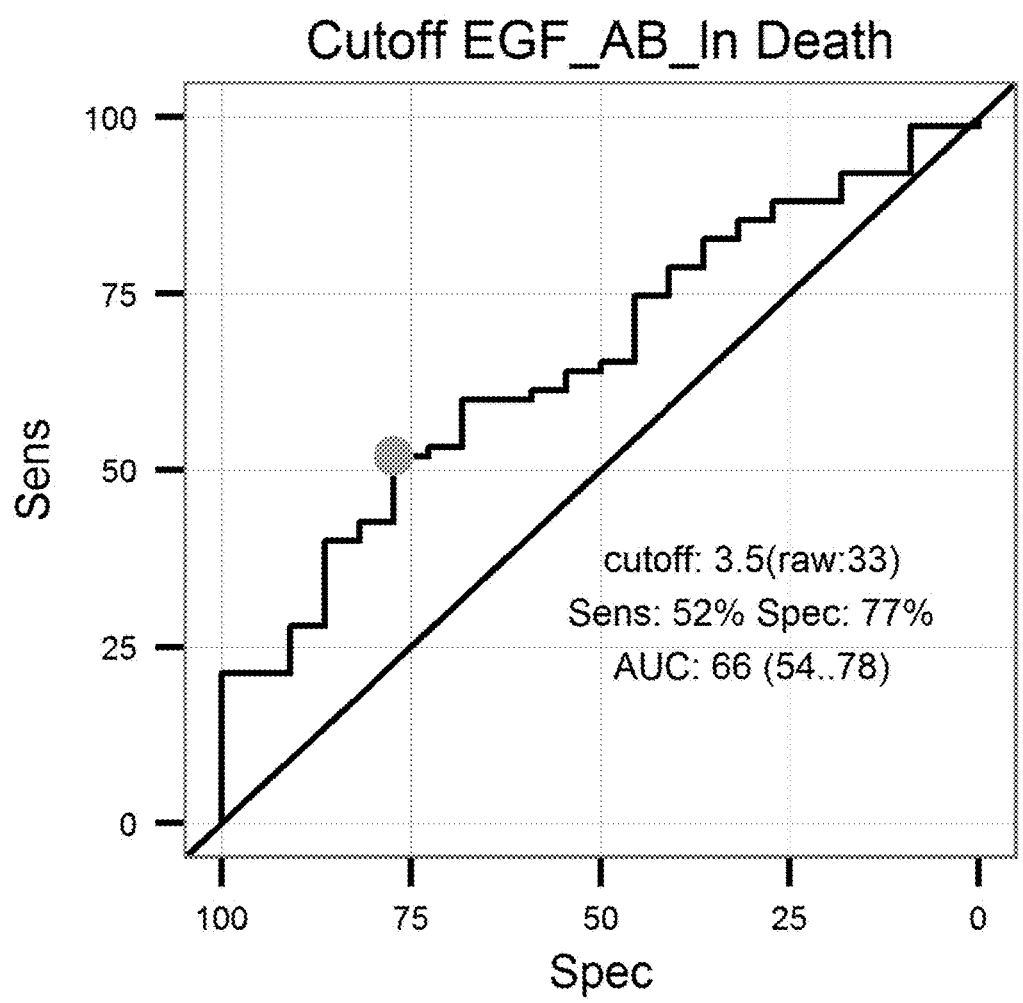
Figure 4:
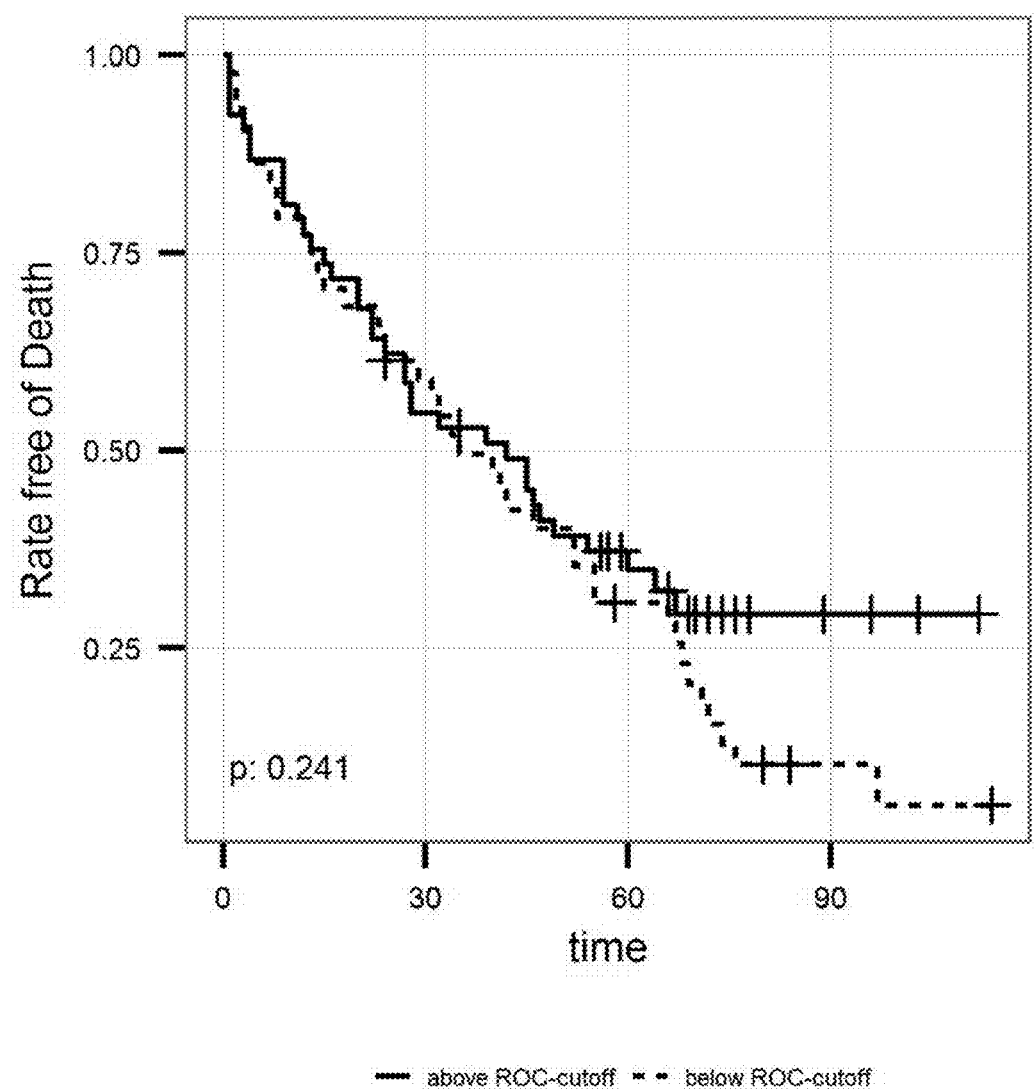
Figure 4:
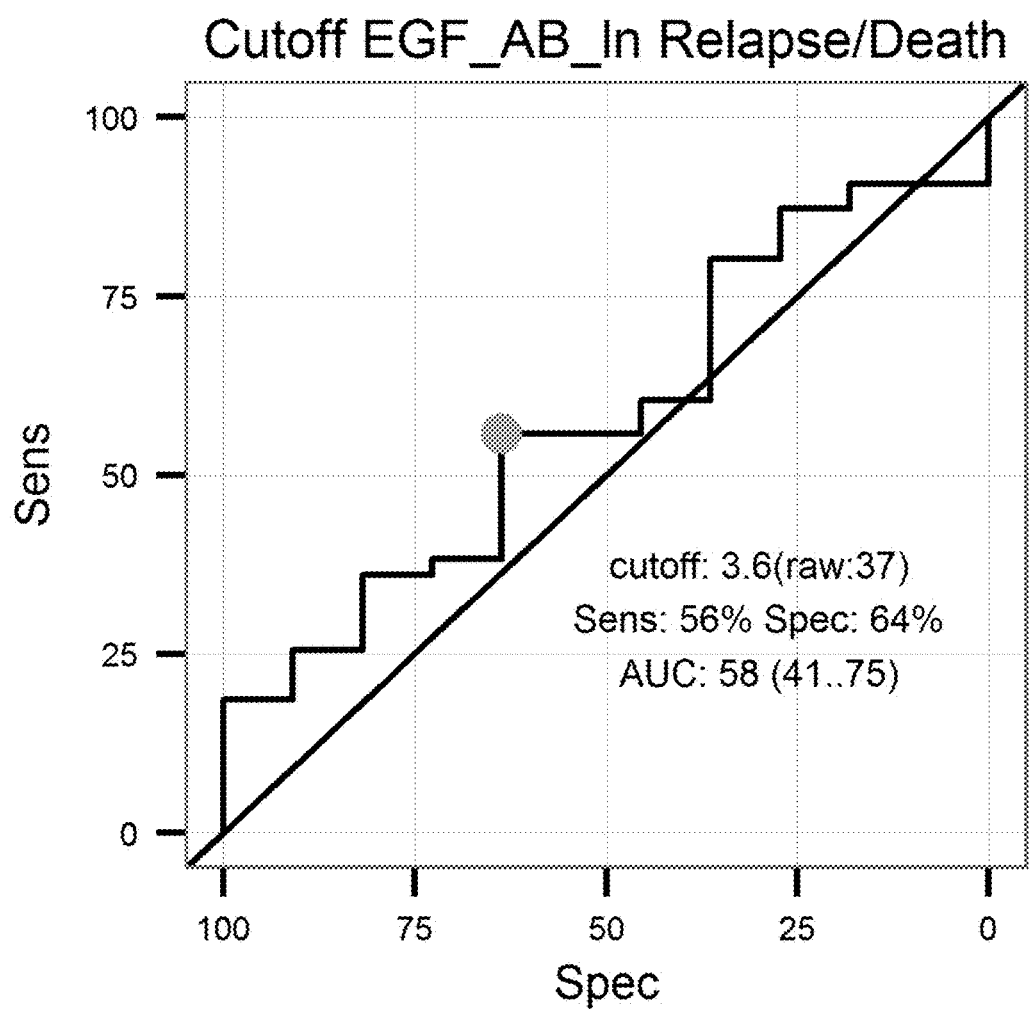
Figure 4:
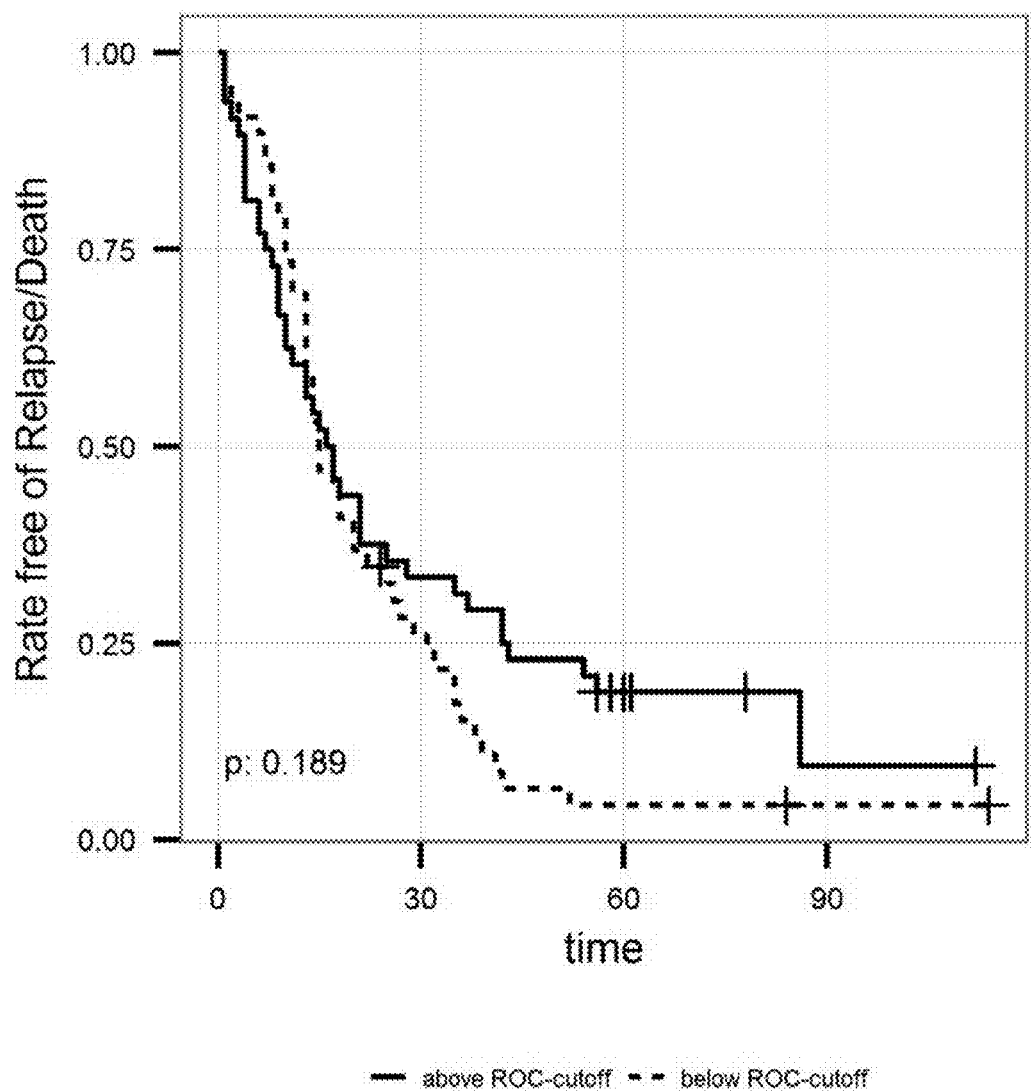

The sensitivity and specificity for levels of anti-EGF antibodies as predictor of relapse and/or mortality after treatment by surgery and platinum analogue was calculated using ROC-analysis. The results for the prediction of relapse are given in FIG. 4A, for the prediction of mortality in FIG. 4B, and for the combined endpoint prediction (relapse or death) in FIG. 4C. The results show that the levels of anti-EGF antibodies are a good predictor for relapse or mortality after treatment of cancer patients as endpoint prediction. The specificity and sensitivity of the prediction could be further enhanced when including further factors in a multivariate model. These factors were age, Figo and histology staging.

The p-value for mortality or the combined end-point (mortality or relapse) was $p<0.001$ and $p<0.011$, respectively in the Cox-proportional hazard. For relapse as the single endpoint we observed a significant value. The p-value was 0.01.

SUMMARY

The results of the present Examples show that anti-EGF antibody levels are significant lower in patients with ovarian cancer compared to healthy controls. Furthermore, the levels are significantly higher in patients in which show no relapse after treatment with panitumumab or chemotherapeutic drugs. Levels of anti-EGF antibody in patients suffering from an ovarian cancer with serous histopathology are higher compared to samples from patients suffering from ovarian cancer with non-serous histopathology. Levels of anti-EGF antibodies in samples are a well suited predictor for the response to the treatment with an inhibitor of EGFR activity. Relapse of cancer or mortality of the patient as endpoints of the treatment with platinum analogues can be predicted with a high degree of specificity and sensitivity.

The invention claimed is:

1. A method for diagnosis and treatment of ovarian cancer, comprising the steps of;

administering, to a subject diagnosed with ovarian cancer, a drug that is an inhibitor of EGF receptor activity, a monoclonal antibody that binds to an EGF receptor, or panitumumab, wherein the ovarian cancer is diagnosed by:

(a) measuring the level of antibodies against epidermal growth factor (EGF) (anti-EGF antibodies) in a serum sample from a subject to be diagnosed, wherein the anti-EGF antibodies bind to recombinant mature EGF of SEQ ID NO:2; and (b) comparing the measured level of anti-EGF antibodies in the sample to a control level of anti-EGF antibodies derived from subjects without cancer;

wherein a decreased level of anti-EGF antibodies in the sample from the subject to be diagnosed as compared to the control level is indicative of ovarian cancer in the subject.

2. The method of claim 1, wherein a level of anti-EGF antibodies below 47 units/ml is indicative of ovarian cancer.

3. The method of claim 1, wherein the anti-EGF antibody is detected in an immunoassay.

4. The method of claim 3, wherein the immunoassay is selected from the group consisting of immunoprecipitation, enzyme immunoassay (EIA), radioimmunoassay (RIA), enzyme-linked immunosorbent assay (ELISA), fluorescent immunoassay, a chemiluminescent assay, an agglutination assay, nephelometric assay, turbidimetric assay, a Western Blot, a competitive immunoassay, a noncompetitive immunoassay, a homogeneous immunoassay a heterogeneous immunoassay, a bioassay and a reporter assay.

5. The method of claim 1, wherein measuring the level of anti-EGF antibodies comprises the steps of:
   (a) contacting the sample with epidermal growth factor (EGF) or an antigenic peptide fragment thereof under conditions allowing for the formation of a complex between anti-EGF antibodies with EGF or a peptide fragment thereof, wherein the anti-EGF antibodies bind to recombinant mature EGF of SEQ ID NO:2; and
   (b) detecting the complex.

6. The method of claim 5, wherein the EGF or the peptide fragment thereof is immobilized on a surface.

7. The method of claim 5, wherein the complex is detected using a secondary antibody against the Fc portion of the anti-EGF antibody.

8. The method of claim 7, wherein the anti-EGF antibody is an IgG-antibody and the secondary antibody is an anti-IgG antibody.

9. The method of claim 8, wherein the secondary antibody is labeled with a detectable marker.

* * * * *